(12) United States Patent
Houston et al.

(10) Patent No.: US 12,268,445 B2
(45) Date of Patent: Apr. 8, 2025

(54) SYSTEMS AND METHODS FOR BINOCULAR VISION EVALUATION AND TREATMENT

(71) Applicant: MASSACHUSETTS EYE AND EAR INFIRMARY, Boston, MA (US)

(72) Inventors: Kevin Houston, Boston, MA (US); Gang Luo, Boston, MA (US)

(73) Assignee: MASSACHUSETTS EYE AND EAR INFIRMARY, Boston, MA (US)

( * ) Notice: Subject to any disclaimer, the term of this patent is extended or adjusted under 35 U.S.C. 154(b) by 554 days.

(21) Appl. No.: 17/620,631

(22) PCT Filed: Jun. 22, 2020

(86) PCT No.: PCT/US2020/038959
§ 371 (c)(1),
(2) Date: Dec. 17, 2021

(87) PCT Pub. No.: WO2020/257771
PCT Pub. Date: Dec. 24, 2020

(65) Prior Publication Data
US 2022/0240773 A1 Aug. 4, 2022

Related U.S. Application Data

(60) Provisional application No. 62/864,011, filed on Jun. 20, 2019.

(51) Int. Cl.
*A61B 3/08* (2006.01)
*A61B 3/00* (2006.01)
*A61B 3/032* (2006.01)
*G16H 15/00* (2018.01)

(52) U.S. Cl.
CPC .............. *A61B 3/08* (2013.01); *A61B 3/0041* (2013.01); *A61B 3/032* (2013.01); *G16H 15/00* (2018.01)

(58) Field of Classification Search
CPC ......... A61B 3/08; A61B 3/0041; A61B 3/032; A61B 3/0033; A61B 3/0058; G16H 15/00; A61H 2205/024; A61H 5/00
USPC .................................................. 351/200, 222
See application file for complete search history.

(56) References Cited

U.S. PATENT DOCUMENTS

| 2010/0283969 A1 | 11/2010 | Cooperstock et al. |
| 2016/0270656 A1 | 9/2016 | Samec et al. |
| 2019/0046029 A1 | 2/2019 | Tomasi et al. |

FOREIGN PATENT DOCUMENTS

WO 2020257771 A1 12/2020

OTHER PUBLICATIONS

International Search Report and Written Opinion issued in corresponding PCT Application No. US2020/038959, issued Sep. 24, 2020.

*Primary Examiner* — Tuyen Tra
(74) *Attorney, Agent, or Firm* — QUARLES & BRADY LLP

(57) ABSTRACT

Systems and methods for treating or detecting binocular vision disorders of a patient. The system, via a display, presents a dichoptic presentation with first and second portions of content that are separated on the display. The first and second portions of content are translated horizontally across the display to adjust the vergence demand of the user.

22 Claims, 23 Drawing Sheets

SYSTEMS AND METHODS FOR BINOCULAR VISION EVALUATION AND TREATMENT

CROSS-REFERENCE TO RELATED APPLICATIONS

This application is a U.S. National Stage of PCT Application No. PCT/US2020/038959 filed on Jun. 22, 2020 which claims priority to U.S. Patent Application No. 62/864,11 filed Jun. 20, 2019, and entitled, "Head-mounted system for allowing doctor to treat and assess binocular vision remotely," which is hereby incorporated by reference in its entirety.

STATEMENT REGARDING FEDERALLY SPONSORED RESEARCH

Not applicable.

BACKGROUND

Binocular vision disorder are fairly common, with occurrences of at least 20% of the general U.S. population and up to 40% of patients seen in clinics. The most common (and easiest to treat) type of binocular vision disorder is Convergence insufficiency ("CI") or poor binocular vision at near distances. This particular disorder occurs in 13% to 17.6% of school age children and 2.3% to 8.5% of the overall U.S. population), and can cause symptoms including eye strain, reduced concentration, problems with sustained near work, and educational disadvantages. Clinical signs of CI can include increased exophoria (eye drifting outwards) at near distances, and either a reduced near point of convergence or a reduced positive fusional convergence.

CI can be treated with binocular vision therapy, which employs visual exercises to improve oculomotor accuracy and endurance during vergence eye movements. Currently, vision therapy for CI requires patients to look at static symbols with different vergence demands. Patients repeat the task multiple times under the supervision of clinicians. The 2008 Convergence Insufficiency Treatment Trial ("CITT"), widely acknowledged for its rigor in study design, found that CI in children was alleviated in 73% of cases with 12 weeks of in-office vision therapy, and successful completion of CI therapy was correlated with improved academic performance. In contrast, other therapy methods studied (in-home computer-based therapy, prism glasses, and home-based pencil push-ups) were no more effective than in-office placebo therapy.

Regarding any CI treatment, patient compliance is a key contributor to successful outcomes. In fact, patient compliance alone has been reported to impact treatment outcomes in vision therapy for CI and amblyopia. Considering that typical treatment protocols are tedious and uninteresting, it can be difficult for practitioners to ensure that their patients are adhering to these programs. Thus, it would be desirable to provide systems and methods for binocular vision evaluation and treatment that can improve patient compliance.

SUMMARY OF THE DISCLOSURE

The present disclosure provides systems and methods for binocular vision evaluation and treatment that overcome the aforementioned drawbacks of typical visual treatment and evaluation systems and methods. As will be described, systems and methods are provided that allow for better compliance for binocular vision treatment and evaluations. As one non-limiting example, the systems and methods provided herein can provide for treatment or evaluation a using television show, a movie, a camera feed, a web browsing application, a 3D scene, virtual reality, augmented reality, an image, a video, a video game, a document, a presentation, a book (or other electronic reading material), and the like.

In some aspects of the disclosure a system for treating or detecting binocular vision disorders of a patient is provided. The system can include a display, a computing device in communication with the display. The computing device can be configured to present to the patient, on the display, a first video that spans a first portion of the display, present to the patient, on the display, a second video that spans a second portion of the display, wherein the first video spanning the first portion of the display does not overlap with the second video spanning the second portion of the display, and wherein the first video spanning the first portion of the display is separated from the second video spanning the second portion of the display to form a dichoptic presentation; and translate the first video on the display to a first different location on the display than the first portion of the display according to a predetermined pattern selected to alter a binocular vergence demand on the patient.

In some aspects of the disclosure a method for treating or detecting binocular vision disorders of a patient is provided. The method can include presenting to the patient, on a display, a first portion of content that spans a first portion on the display, presenting to the patient, on the display, a second portion of content that spans a second portion of the display, wherein the first portion of content spanning the first portion of the display does not overlap with the second portion of content spanning the second portion of the display, and wherein the first portion of content spanning the first portion of the display is separated from the second portion of content spanning the second portion of the display to form a dichoptic presentation, translating the first portion of content, on the display, to a first different location on the display than the first portion of the display according to a predetermined pattern selected to alter a binocular vergence demand on the patient, and translating the second portion of content, on the display, to a second different location on the display than the second portion of content on the display according to the predetermined pattern selected to alter the binocular vergence demand on the patient.

In some aspects of the disclosure a non-transitory computer-readable medium storing computer-executable code, comprising code is provided. The code can cause a computing device to present to a patient, on the display, a first portion of content that spans a first portion of the display, present to the patient, on the display, a second portion of content that spans a second portion of the display, wherein the first portion of content does not overlap with the second portion of content, and wherein the first portion of content and the second portion of content form a dichoptic presentation, translate the first portion of content on the display according to a predetermined pattern selected to alter a binocular vergence demand on the patient, and translate the second portion of content on the display according to the predetermined pattern selected to alter a binocular vergence demand on the patient. In some aspects, the first portion of content and the second portion of content are substantially identical.

The foregoing and other aspects and advantages of the disclosure will appear from the following description. In the description, reference is made to the accompanying drawings which form a part hereof, and in which there is shown by way of illustration a preferred configuration of the disclosure. Such configuration does not necessarily represent the full scope of the disclosure, however, and reference is made therefore to the claims and herein for interpreting the scope of the disclosure.

BRIEF DESCRIPTIONS OF THE DRAWINGS

DETAILED DESCRIPTION

Figure 1:
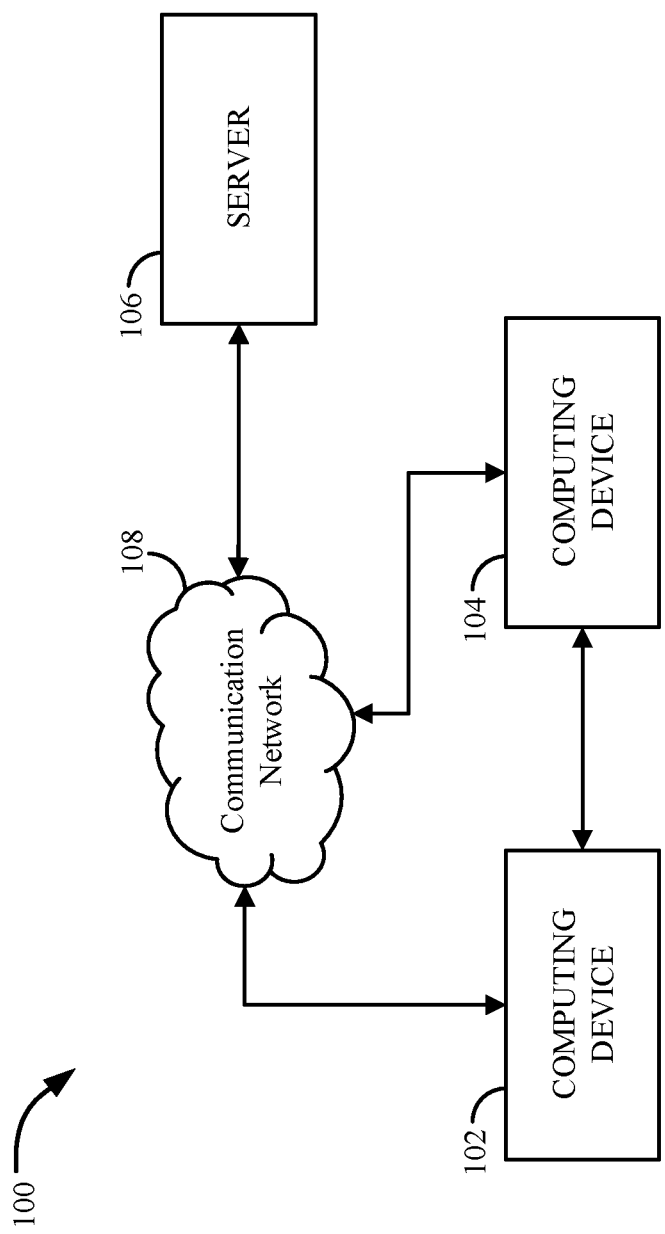
FIG. 1 shows a block diagram of a binocular vision disorder system for the evaluation or treatment of binocular vision disorders in accordance with the present disclosure.

As detailed above, while some binocular vision disorders have been successfully treated with visual exercises that require the patient to look at static targets with augmented vergence demands, practitioners often have difficulties with patients failing to adhere to these programs. For example, these exercises can be difficult, tedious, and lengthy, all of which can attribute to the patient failing to stay regimented with the program. Additionally, these factors can be exacerbated as children generally have significantly shorter attention spans (as compared to adults). As a more specific example, an in-home therapy system such as the HTS@ desktop computer system was evaluated in the CITT study and showed that patient compliance rates were substantially lower than in-office therapy. The tedious and boring monochromatic nature of the HTS@ at-home training exercises, combined with the lack of doctor assessment during training, likely contributed to the reduced compliance and efficacy.

While in-office vision therapy can allow for better adherence or compliance to the vision therapy exercises, there are still issues with the in-office approach. For example, access to in-office therapy can be severely limited by direct barriers including high direct patient costs (most vision therapy practices do not accept insurance), and the significant time commitment (e.g., multiple visits per week for several weeks). These direct barriers can also cause indirect costs, such as lost time at school and work. Thus, it is not surprising that these barriers can cause many binocular vision cases to go untreated or ineffectively treated, which can force these patients to live with issues associated with these conditions.

Some non-limiting examples of the disclosure provide improved systems and methods for binocular vision evaluation and treatment. For example, some non-limiting examples of the disclosure provide a binocular vision disorder treatment (or evaluation) system that is configured to present, on a display, a dichoptic view of two images (videos, webpage content, and the like). The vergence demand of the user is adjusted by translating the images (or other content) toward each other, or away from each other, according to a predetermined pattern. This predetermined pattern can include relatively fast translations (e.g., impulses that may not be actively tracked by the user's eye, such as less than 0.0167 seconds corresponding to 60 Hz) followed by periods of waiting and non-movement of the images (or other content). This predetermined pattern can, over a treatment session, cause the user's eyes to gradually converge and diverge to a large amplitude without causing visual discomfort (e.g., double vision), which can signal that the user is improving. Additionally, in some cases, the user can interact with the system to notify if the user is experiencing discomfort, and based on the system receiving a user input indicating discomfort, the system can decrease the vergence demand on the user. This system can be particularly advantageous for a few reasons. First, the user can select any type of content that's desired for the treatment session (e.g., television shows, movies, live or recorded camera feeds, web browsing, and the like), which alone can greatly increase compliance (e.g., the user can be treated while doing leisurely activities). Second, the user can complete the treatment session at home, and thus does not need to routinely go to the doctor's office to complete the treatment session (e.g., which can save on costs, and time). Third, the practitioner can remotely adjust, track, and augment the predetermined pattern to tailor a treatment plan to the specific user.

FIG. 1 shows a schematic illustration of a binocular vision disorder system 100 for the evaluation or treatment of binocular vision disorders. The system 100 includes a computing device 102 that, as will be described, is able to display a visual representation to a patient and translate the visual representation according to a predetermined pattern selected to alter a binocular vergence demand on the patient. In addition to the computing device 102, the system 100 may, optionally, include another computing device 104, and a server 106, which can all communicate with each other via the communication network 108. In some cases, and as shown, the computing device 102 can directly communicate with the second, optional computing device 104. The communication abilities of the computing devices 102, 104, and the server 106 can include the transmission (and receiving) of data, instructions, and the like, between each other. For example, in some configurations, the patient can run any software he owns on the computing device 104 (e.g. video game, social media, office work, online shopping, reading news). In this case, the display 132 of the computing device 104 is casted to the computing device 102 in real time and presented as a dichoptic view to the patient using the disclosed hardware, firmware, or software in the computing device 102. Additionally, the computing device 102 can relay data (e.g., treatment session run-time, number of breaks, and the like) to the server 106 so that the practitioner can access, evaluate and analyze the data to adjust the predetermined pattern.

In some non-limiting examples, the computing devices 102, 104, and the server 106 can take any of a variety of forms, including traditional "computer" systems (rack-mounted, desktop or laptop), mobile device (tablet or phone), and/or dedicated device. In this way, the computing devices 102, 104 can include a processor, memory, communication systems, a display, inputs (e.g., a mouse, a keyboard, touch screen or the like, to provide a user input), while the server 106 can include processors, memory, power sources (e.g., power supplies), communication systems, and the like.

Figure 2:
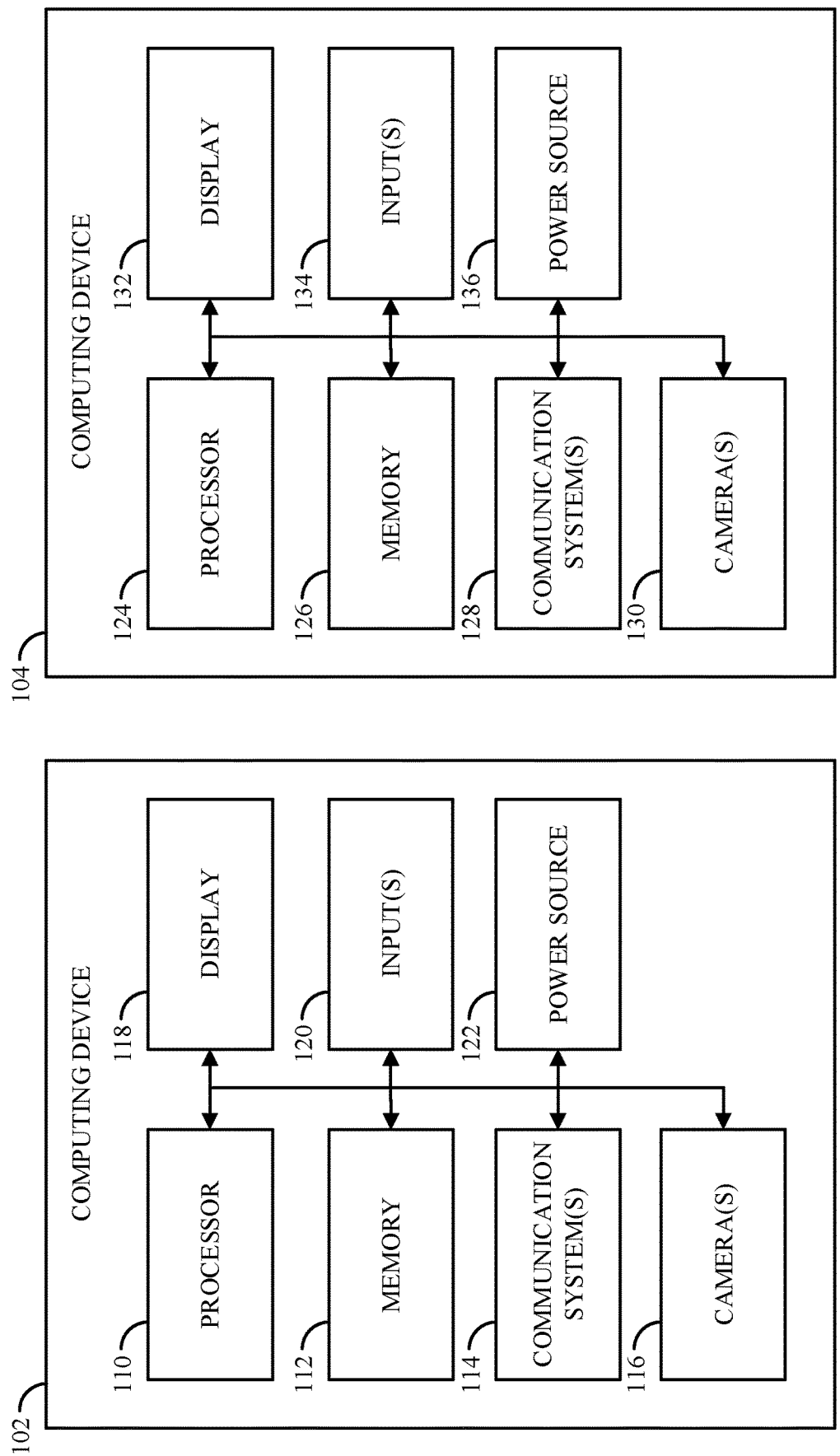
FIG. 2 shows a schematic illustration of an example of specific implementations of the computing devices of the binocular vision disorder system of FIG. 1.

FIG. 2 shows schematic illustrations of an example of specific implementation of the computing devices 102, 104. The computing device 102 can include a processor device 110, memory 112, communication system(s) 114, a camera 116, displays 118, inputs 120, and a power source 122. The processor device 110 can control specific features of the computing device 102, such as presenting content (e.g., images, videos, and the like) on the display 118. As another example, the processor device 110 can implement some or all of the processes (or methods) described in the present disclosure. The processor device 110 can be any suitable hardware processor or combination of processors, such as a central processing unit ("CPU"), a graphics processing unit ("GPU"), and the like, which can execute a program (e.g., retrieved from memory 112), including for one or more of the processes described below.

In some non-limiting examples, the computing device 102 can include memory 112. The memory 112 can include any suitable volatile memory, non-volatile memory, storage, or any suitable combination thereof. For example, the memory 112 can include random-access memory ("RAM"), static random-access memory ("SRAM"), read-only memory ("ROM"), electrically erasable programmable read-only memory ("EEPROM"), one or more flash drives, one or more hard disks, one or more solid state drives, one or more optical drives, and the like In some non-limiting examples, the memory 112 can have encoded thereon a computer program for controlling operation of the processor device 110, including as may be interpreted and executed by the processor device 110 to control other devices. For example, the memory 112 can store a program that includes the current predetermined pattern, which controls how the display presents the specific content.

The one or more communication system(s) 114 can include any suitable hardware, firmware, or software for communicating with components external to the computing device 102, including, for example, a communication system within the motorcycle, a smartphone, a global positioning system, and the like For example, the communications system(s) 114 can include one or more transceivers, one or more communication chips or chip sets, and the like In a more particular example, communications system(s) 114 can include hardware, firmware or software that can be used to establish a coaxial connection, a fiber optic connection, an Ethernet connection, a universal serial bus ("USB") connection, a Wi-Fi connection, a Bluetooth connection, a cellular connection, a serial interface connection, and the like In some non-limiting examples, the computing device 102 can include cameras 116 to acquire imaging data of the user. For example, the cameras 116, which can each include an imaging sensor, lenses, prisms, and the like, can acquire images of sports games, lectures, concerts or TV screens. In this case, the acquired images will be presented to the patient in dichoptic view for treatment.

In some non-limiting examples, the display 118 can present a graphical user interface. In some non-limiting examples, the display 318 can be implemented using any suitable display devices, such as a monitor, a touchscreen, a television, and the like In some specific non-limiting examples, the display can be a liquid crystal display ("LCD"), an organic light-emitting diode ("OLED"), and the like In some non-limiting examples, such as in particular with regard to when the computing device 102 is implemented as glasses (e.g., smart glasses), virtual reality goggles, or other types of eyewear, each of the displays can present an image (or other content) to a respective eye of the subject to generate a dichoptic presentation to the user.

In some non-limiting examples, the display 118 can include lenses that can facilitate the dichoptic presentation to the user. For example, the display 118 can include a lens positioned in front of the display 118, and which can project the dichoptic presentation to the user. In particular, the display 118 can present a first portion of content on one side of the display 118 and a second portion of content on the opposite (horizontal) side of the display. With respect to the patient, the first portion of content (presented on the display 118) is projected through the lens and to only the left eye of the patient, while the second portion of content (presented on the display 118) is projected through the lens and to only the right eye of the patient. As another example, the display 118 can include a first lens positioned in front of the display 118 on the one side of the display 118, and a second lens positioned in front of the display 118 on the one side of the display 118. In this case, both the first lens and the second lens can be positioned the same distance away from the display 118, and can be identical in optical properties (e.g., magnification). This way, with respect to the patient, the first portion of content (presented on the display 118) is projected through the first lens and to only the left eye of the patient, while the second portion of content (presented on the display 118) is projected through the second lens and to only the right eye of the patient. It can be appreciated that the lenses can be mounted in different ways, such as a frame of glasses, secured within head mounted goggles, etc.

In some non-limiting examples, the inputs 120 of the controller device 102 can include actuatable buttons, a keyboard, a mouse, a graphical user interface, a touch-screen display, and the like, to provide a user input to the controller device 102. In some non-limiting examples, the inputs 120 can include indicators (e.g., light emitting diodes ("LEDs")), sensors, data-in pins/connections, data-out pins/connections, and the like In some non-limiting examples, the power source 122, as appropriate, can supply power to all of the components of the computing device 102. Thus, the power source 122 can be implemented in different ways, including being a hard-wired connection, an electrical storage device (e.g., a battery) and the like In some non-limiting examples, the computing device 102 can be implemented in many different ways. For example, the computing device 102 can be a smartphone, a tablet, or other hand-held display device that can be interfaced with a head mounting device. In this case, the display 118 of the computing device 102 can be used as the display of the head mounting device to create a head mounted display. As another example, the computing device 102 can be implemented as various eyewear displays, such as smart glasses, virtual reality goggles, and the like In these cases, when the computing device 102 forms part of an eyewear device, the computing device 102 can have one display 118 solely for presenting content to one of the user's eyes, and another display 118 solely for presenting content to the other user's eye. As yet another example, the computing device 102 can be a personal computer (e.g., a laptop). In some non-limiting examples, when the computing device 102 is implemented as being secured to the head of the subject (e.g., a head mounted device, eye wear, and the like), the inputs 120 can include movement sensors (e.g., an accelerometer). For example, the user moving their head can be effectively used as a cursor to navigate a menu. Similarly, by rotating their head, the computing device 102 can determine that the user is experiencing some degree of discomfort.

As shown in FIG. 2, the computing device 102 can also include a processor 124, memory 126, communication system(s) 128, cameras 130, displays 132, inputs 134, and a power source 136. Considering that the computing device 102 includes similar components as the computing device 104, the descriptions of these components with regard to the computing device 104 also applies to these components of the computing device 104. In some configurations, the computing devices 102, 104 can be a personal computer, a smart phone, a desktop computer, and the like.

Figure 3:
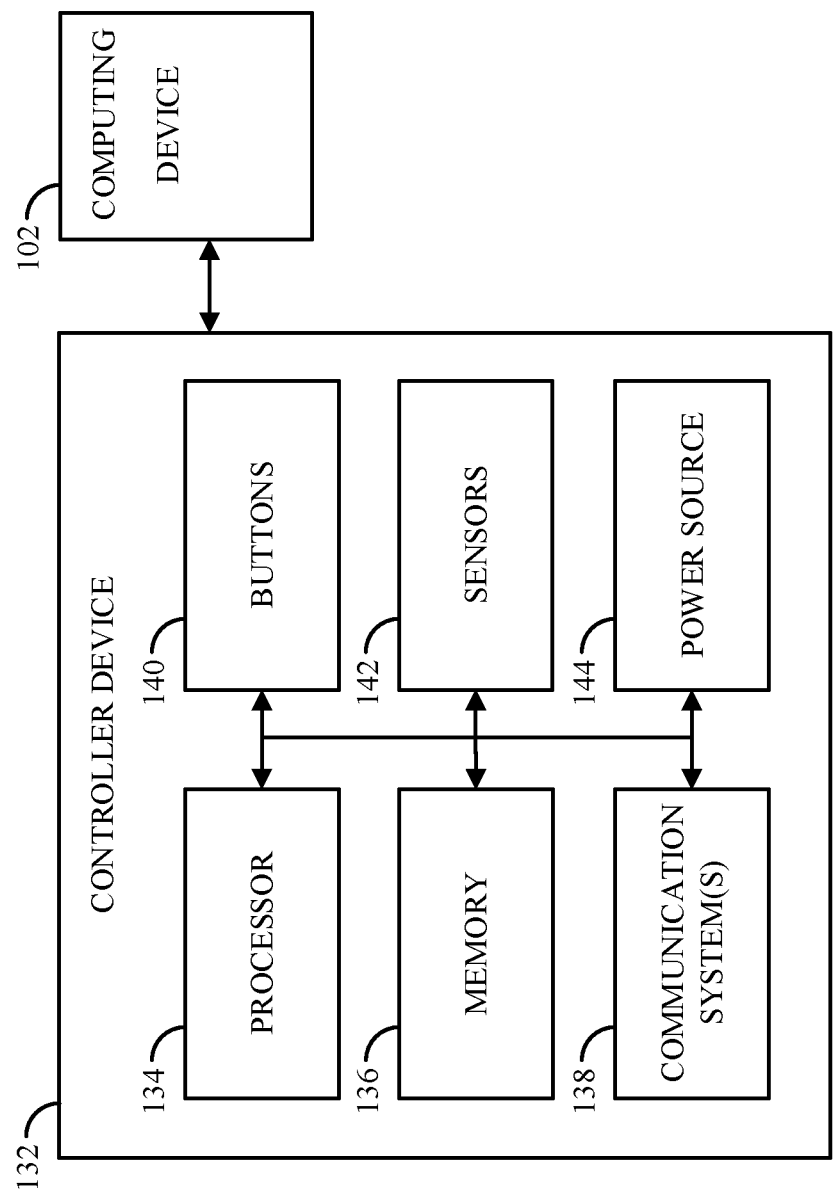
FIG. 3 shows another schematic illustration of a controller device in communication with the computing device of FIG. 1.

Referring to FIG. 3, in some non-limiting examples, the computing device 102 can include or communicate with a controller device 132 for user communication with the computing device 102. The controller device 132 can include a processor 134, memory 136, communication system(s) 138, actuatable buttons 140, sensors 142, a power source 144, and the like. The actuatable buttons 140 can be tied to a particular state of the user. For example, the actuatable buttons 140 can include a "break" indicator, and a comfortability indicator, that when depressed (e.g., by a user experiencing the particular state), is transmitted by the controller device 132 to be received by the computing device 102. In some cases, the actuatable buttons 140 can include vergence demand modifier buttons. For example, the actuatable buttons 140 can include an increase (and decrease) vergence demand button, and an increase (and decrease) vergence frequency button that when depressed, transmits a command from the controller device 132 to be received by the computing device 102 to modify the predetermined pattern, which adjusts the vergence demand on the subject.

In some non-limiting examples, the sensors 142 can include motion sensors (e.g., accelerometers, gyroscopes, and the like) that can determine a particular movement pattern, orientation change, and the like of the user to adjust the operation of the computing device 104. For example, when the user provides reciprocated motion (or a different movement pattern) to the controller device 132, the controller device 132 can cause the computing device 104 to adjust its operation (e.g., to indicate the fusion-breakpoint for the user). In some non-limiting examples, the sensors 142 can include a joystick or other movable interface that can adjust the location of a cursor presented on the display 118 of the computing device 104 so that the user can appropriately navigate a menu.

Figure 4:
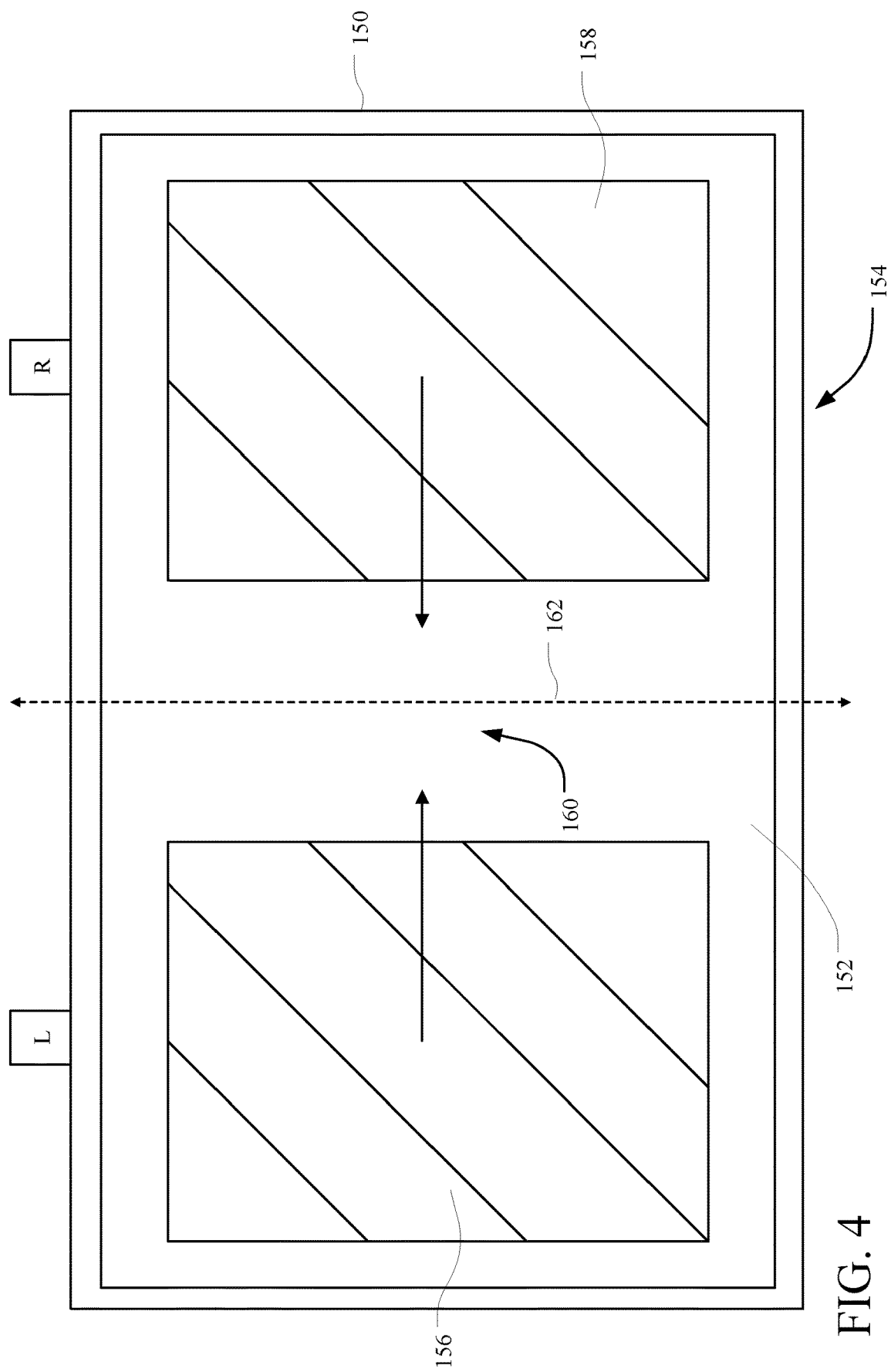
FIG. 4 shows an illustration of a display presenting a dichoptic presentation to the user in accordance with the present disclosure.

FIG. 4 shows an illustration of a display 150 (in a landscape view) presenting a dichoptic presentation to the user. The display 150 is a specific implementation of the display 118, and thus the display 150 is implemented as being part of the computing device 102. The display 150 defines a display surface 152, which is portion of the display 150 that visibly changes to the user (e.g., the portion of the display 150 with the array of light emitting elements, or in other words the array of pixels). As shown, the display 150 is presenting a dichoptic presentation 154 to the user, which includes a first portion of content 156 on a left side of the display 150 and a second portion of content 158 on the right side of the display 150. The first portion of content 156 defines a first area (or region) on the display 150, and the second portion of content 158 defines a second area (or region) on the display 150. As shown, the first area of the first portion of content 156 and the second area of the second portion of content 158 are substantially (e.g., deviating by less than 10%) similar in size and shape. The first portion of content 156 and the second portion of content 158 are separated from each other by a horizontal distance 160. Thus, in the dichoptic presentation 154 the first portion of content 156 does not overlap with the second portion of content 158. Additionally, in some non-limiting examples, the display 150 can define a vertical axis 162 that bisects the display 150 and the display surface 152. In some configurations, the first portion of content 156 is horizontally separated from the vertical axis 162 by a horizontal distance that is substantially similar to a horizontal distance that separates the second portion of content 158 from the vertical axis 162. Although the first portion of content 156, and the second portion of content 158 is illustrated as being rectangles, in other configurations other shapes are contemplated, including circles, ovals, and the like. Additionally, although much of the description below will describe the portions of content 156, 158 translating horizontally, it can be appreciated that the portions of content 156, 158 (and others) can translate vertically according to the predetermined pattern of movement (e.g., with the same magnitudes of movement), which can be used to detect or treat vertical phoria.

Figure 5:
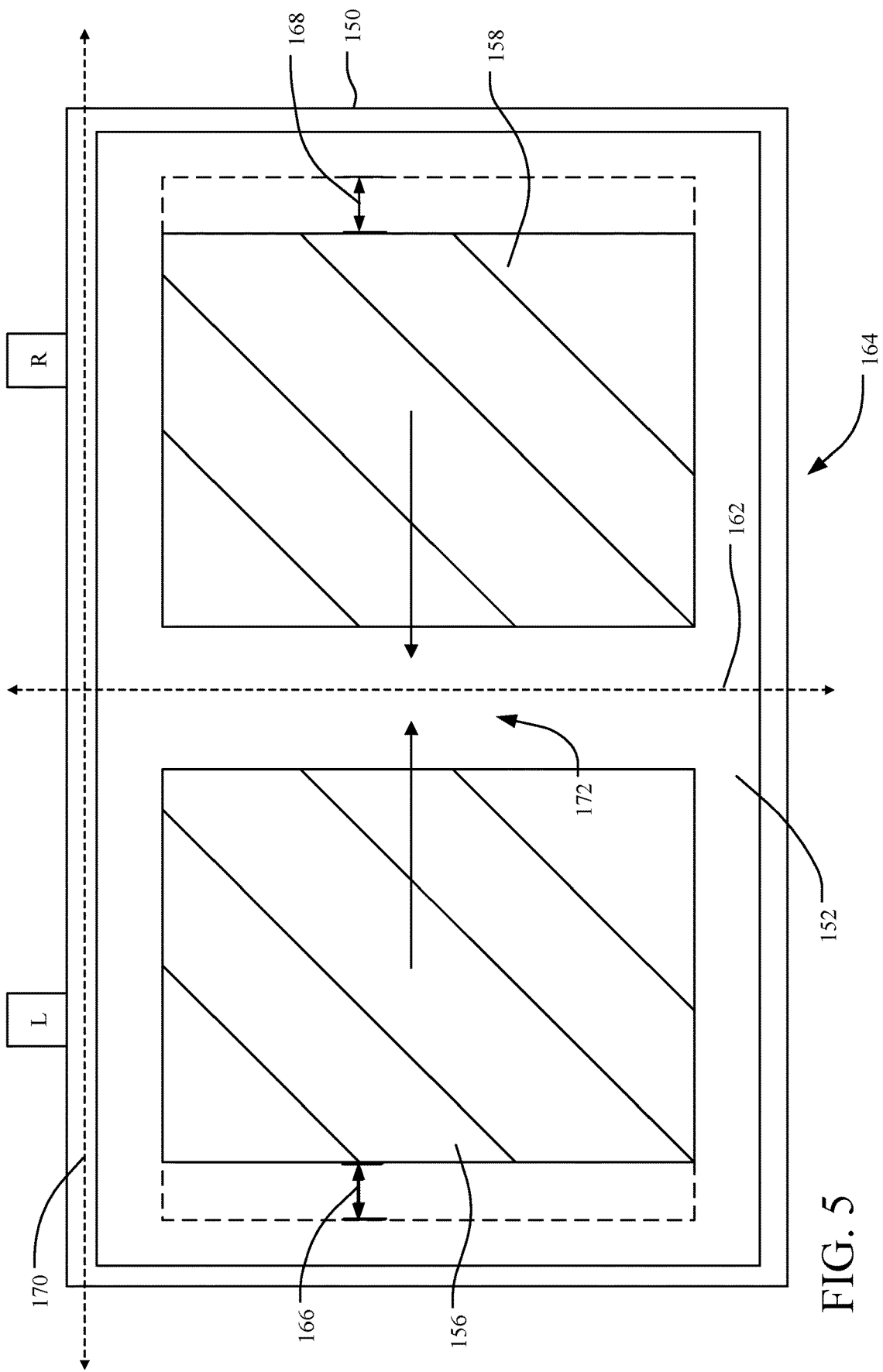
FIG. 5 shows an illustration of the display of FIG. 4 presenting another dichoptic presentation to the user.

FIG. 5 shows an illustration of the display 150 presenting another dichoptic presentation 164 to the user. The dichoptic presentation 164 increases the vergence demand of the user, and more specifically increases convergence demand of the user (e.g., when compared to the dichoptic presentation 154). As shown, the dichoptic presentation 164 includes the first portion of content 156 that has been translated to a different location on the display surface 152 towards the vertical axis 162 by a horizontal distance 166. Similarly, the dichoptic presentation 164 includes the second portion of content 158 that has been translated to a different location on the display surface 152 towards the vertical axis 162 by a horizontal distance 168. As shown, the magnitudes of the horizontal distances 166, 168 are substantially similar, while the translation directions of the horizontal distances 166, 168 are opposite. In other words, the display 150 can define a horizontal axis 170 and the first portion of content 156 is translated along the horizontal axis 170 in a direction towards the vertical axis 162, while the second portion of content 158 is translated along the horizontal axis 170 in an opposite direction towards the vertical axis 162. As shown in FIG. 5, in the dichoptic presentation 164 the first portion of content 156 is separated from the second portion of content 158 by a horizontal distance 172, and thus the first portion of content 156 does not overlap with the second portion of content 158.

When comparing FIGS. 4 and 5, the horizontal distance 160 that separates the first and second portions of content 156, 158 in the dichoptic presentation 154 is larger than the horizontal distance 172 that separates the first and second portions of content 156, 158 in the dichoptic presentation 164. In other words, the horizontal distance 172 is smaller than the horizontal distance 160. This translation of the first and second portions of content 156, 158 increases the convergence demand on the user (e.g., causes the users eyes to simultaneously move toward each other to maintain binocular vision by the user appropriately fusing the first and second portions of content 156, 158 together).

Figure 6:
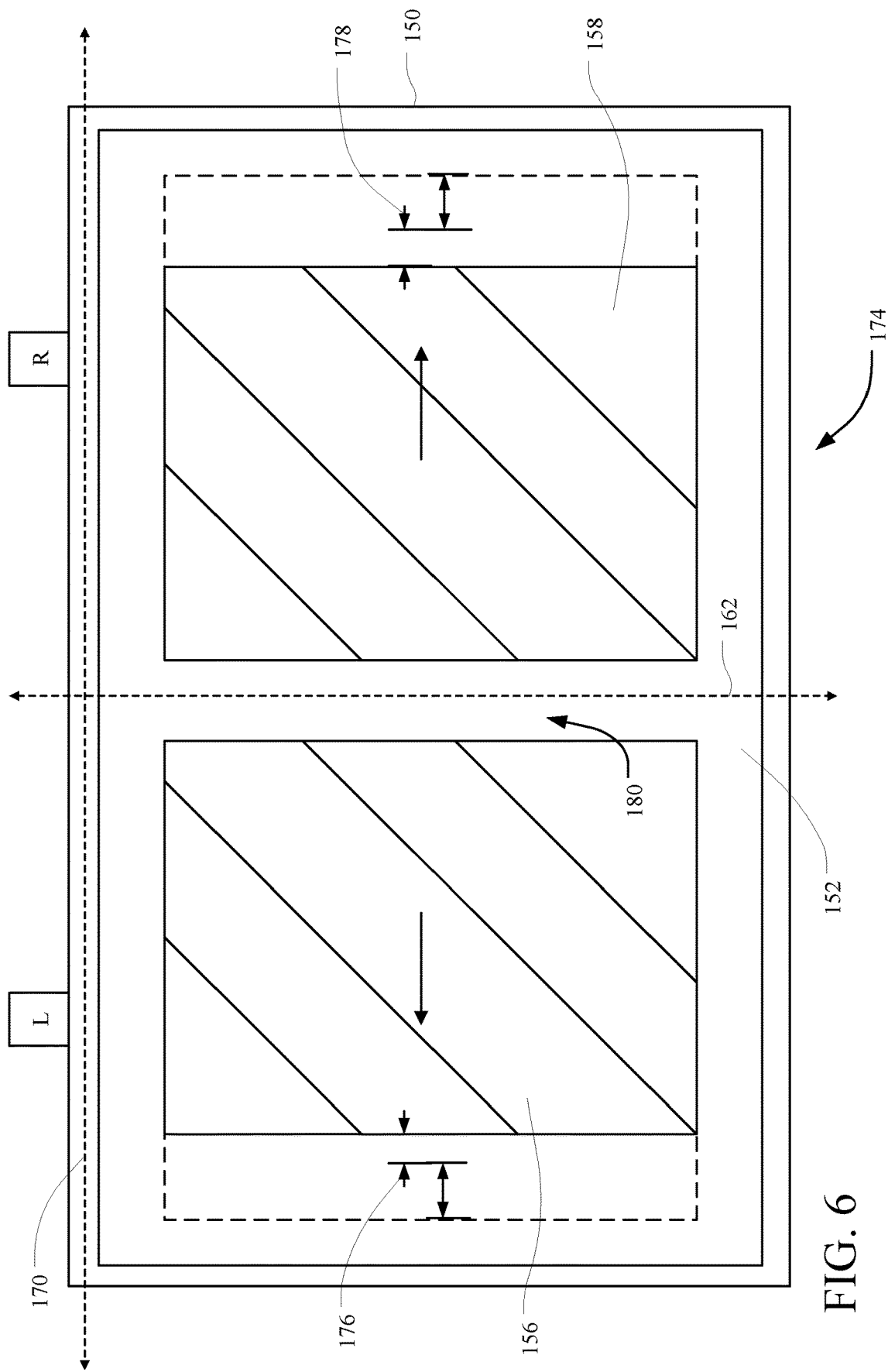
FIG. 6 shows an illustration of the display of FIG. 4 presenting another dichoptic presentation to the user.

FIG. 6 shows an illustration of the display 150 presenting another dichoptic presentation 174 to the user, which further increases the convergence demand of the user (e.g., when compared to the dichoptic presentations 154, 164). As compared to the dichoptic presentation 164, the dichoptic presentation 174 includes the first portion of content 156 being further translated to another different location on the display surface 152 towards the vertical axis 162 by a horizontal distance 176 (and the first portion of content 156 being translated along the horizontal axis 170 along a first direction). Similarly, the dichoptic presentation 174 includes the second portion of content 158 that has been further translated to another different location on the display surface 152 towards the vertical axis 162 by a horizontal distance 176, 178 (and the second portion of content 158 being translated along the horizontal axis 170 along a second direction opposite the first direction). As shown, the magnitudes of the horizontal distances 176, 178 are substantially similar. Additionally, as shown in FIG. 6, in the dichoptic presentation 174, the first portion of content 156 is separated from the second portion of content 158 by a horizontal distance 180, and thus the first portion of content 156 does not overlap with the second portion of content 158. When comparing FIGS. 4, 5, and 6 the horizontal distance 180 is smaller than the horizontal distances 160, 172, and thus the dichoptic presentation 174 having the horizontal distance 180 increases the convergence demand of the user.

Figure 7:
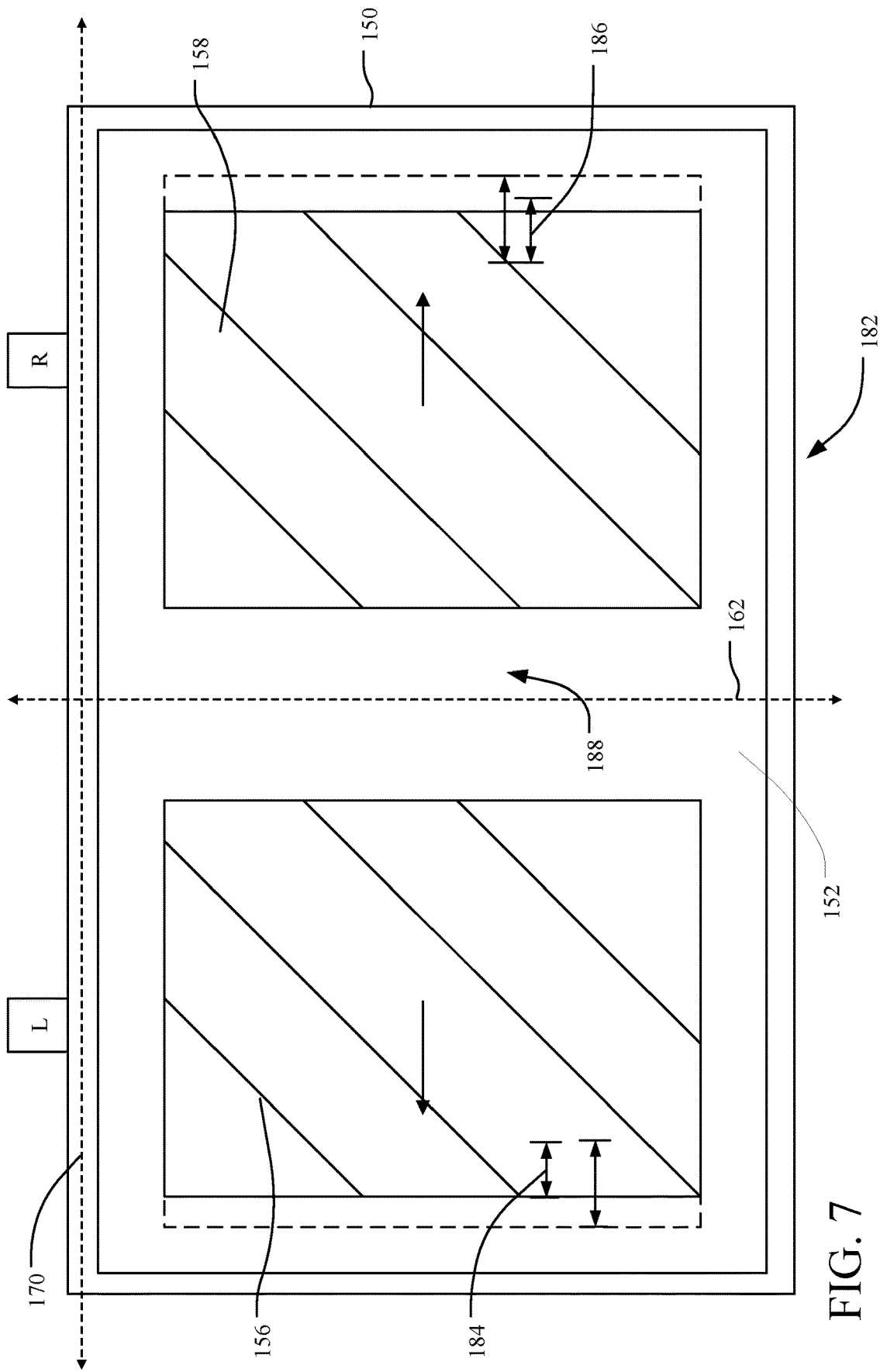
FIG. 7 shows an illustration of the display of FIG. 4 presenting another dichoptic presentation.

FIG. 7 shows an illustration of the display 150 presenting another dichoptic presentation 182, which increases the divergence demand of the user (e.g., when compared to the dichoptic presentation 174). As compared to the dichoptic presentation 174, the first portion of content 156 is translated away from the vertical axis 162 to a different location on the display surface 152 by a horizontal distance 184 (and the first portion of content 156 being translated along the horizontal axis 170 along the second direction). Similarly, the dichoptic presentation 182 includes the second portion of content 158 being translated away from the vertical axis 162 to a different location on the display surface by a horizontal distance 186 (and the first portion of content 156 being translated along the horizontal axis 170 along the second direction). As shown, the magnitudes of the horizontal distances 184, 186 are substantially similar. Additionally, as shown in FIG. 7, in the dichoptic presentation 182, the first portion of content 156 is separated from the second portion of content 158 by a horizontal distance 188 (and thus the first portion of content 156, and the second portion of content 158 do not overlap). Due to the horizontal distance 188 being greater than the horizontal distance 180 the divergence demand for the user is greater in the dichoptic presentation 182 than the dichoptic presentation 174. Similarly, due to the horizontal distance 180 being smaller than the horizontal distance 188 the convergence demand for the user is greater in the dichoptic presentation 174 than the dichoptic presentation 182.

In some non-limiting examples, the first portion of content 156 and the second portion of content 158 can be substantially similar (or identical). In other words, the first portion of content 156 and the second portion of content 158 can be derived from the same source (e.g., being the same image). In other cases, as will be described below, the first portion of content 156 and the second portion of content 158 can be the same but with one region of the first or second portions of content 156, 158 occluded (e.g., the region that corresponds to the user's amblyopia eye), or in other words not displaying.

In some non-limiting examples, the first portion of content 156, and the second portion of content 158 can be a television show, a movie, a camera feed, a web browsing application, a 3D scene (e.g., when implemented as a virtual reality headset), an image, a video (generally), a video game, a document, a presentation, a book (or other electronic reading material), and the like. In some cases, the first portion of content 156 and the second portion of content 158 can be retrieved from memory (e.g., memory 112), while in other cases, the first portion of content 156 and the second portion of content 158 can be screencasted to the computing device 102 from the computing device 104 (e.g., if the computing devices 102, 104 are running the same software and connected to the same WiFi, or other, network). In some non-limiting examples, the computing device 102 can stream the first portion of content 156 and the second portion of content 158 from a server (e.g., the server 106) via a communication network (e.g., the communication network 108). In some configurations, the computing device 102 can receive a given piece of content (e.g., from memory, a server, another computing device, and the like) and can duplicate the piece of content to then present, on the display, the first portion of content 156 and the second portion of content 158 (e.g., both being derived from the given piece of content).

In some non-limiting examples, when the computing device 102 presents a dichoptic view (e.g., the dichoptic view 182) there are regions on the display surface 152 that do not contain the first portion of content 156 or the second portion of content 158. These regions can be visually activated (e.g., with a single uniform color, such as white), or in other cases, these regions do not need to be visually activated, such that these regions take on the optical characteristics of a non-visually activated display screen (e.g., being a black color). In some cases, having a uniform color throughout these regions can allow for better therapy regiments for the user (e.g., the user is not distracted by the surrounding regions).

Figure 8:
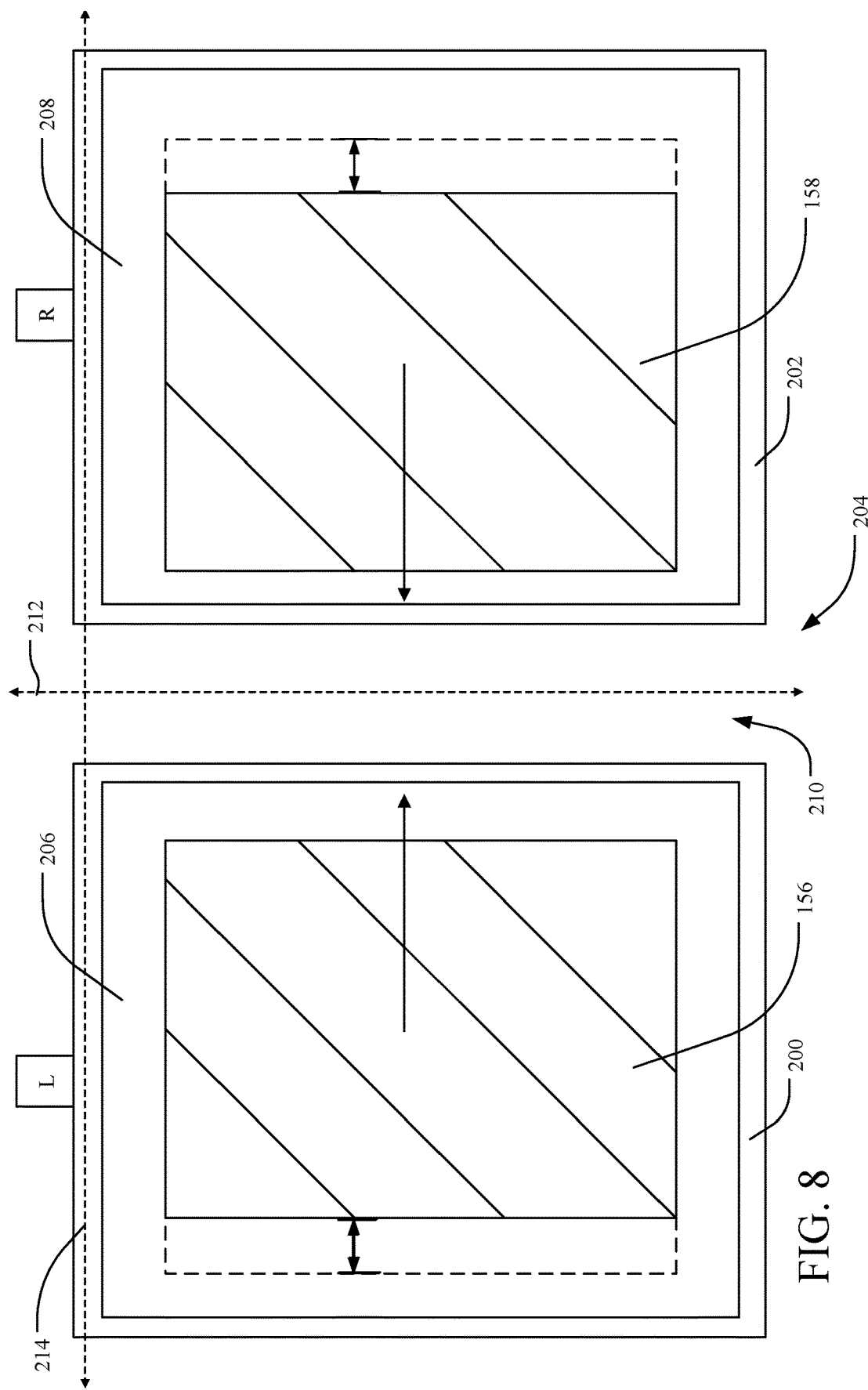
FIG. 8 shows displays presenting a dichoptic presentation to a user in accordance with the present disclosure.

Although the dichoptic presentations above with regard to FIGS. 4-7 are shown presented on a single display 150, with the first portion of content 156 intended for viewing by only the user's left eye and with the second portion of content 158 intended for viewing by only the user's right eye, in alternative non-limiting examples multiple displays can be utilized. For example, FIG. 8 shows displays 200, 202 presenting a dichoptic presentation 204 to the user. The displays 200, 202 are a specific implementation of the display 118, and thus the computing device 102 can cause content to be presented on the displays 200, 202 to the user. As shown, the display 200 has a display surface 206 that is presenting the first portion of content 156, while the display 202 has a display surface 208 that is presenting the second portion of content 158. The displays 200, 202 are physically separated by a horizontal distance 210, where a vertical axis 212 bisects the horizontal distance 210 into two equal horizontal distances. Similarly to the display 150, the display 200 is configured to translate the first portion of content 156 horizontally (e.g., along the horizontal axis 214 that is perpendicular to the vertical axis 212) toward the vertical axis 212 (to increase the convergence demand on the user), or away from the vertical axis 212 (to increase the divergence demand on the user). The display 202 is also configured to translate the second portion of content 158 horizontally (e.g., along the horizontal axis 214) toward the vertical axis 212 (to increase the convergence demand on the user), or away from the vertical axis 212 (to increase the divergence demand on the user).

Figure 9:
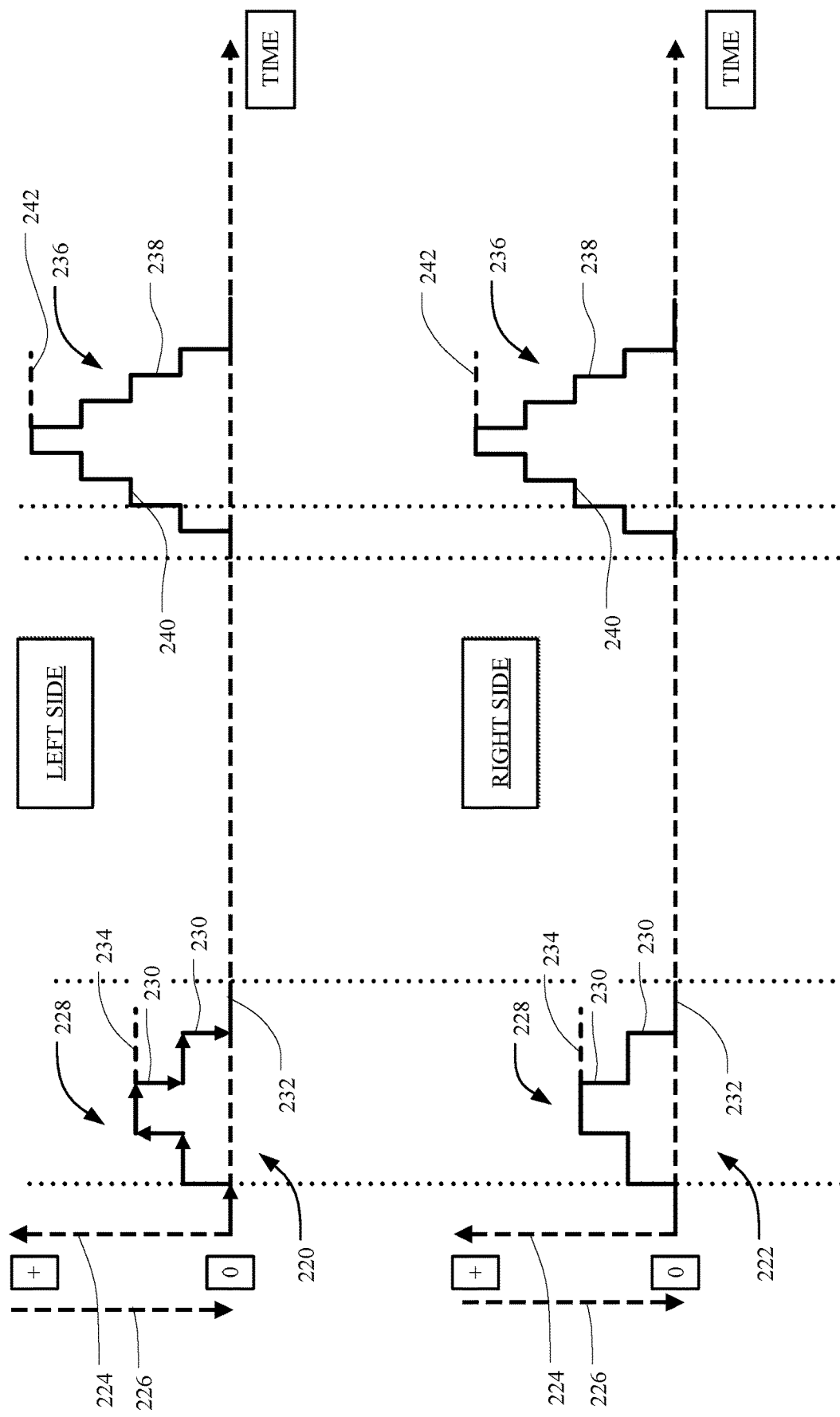
FIG. 9 shows graphs having predetermined patterns of movement that adjust the vergence demand of a user in accordance with the present disclosure.

FIG. 9 shows graphs 220, 222 of predetermined patterns of movement that adjust the vergence demand of a user. As shown, the graph 220 is only for the left side of the user (e.g., for viewing with only the left eye), and has time for one axis (e.g., in minutes) verses horizontal translational movement relative to a neutral position "0". As the graph moves from the neutral portion in a positive direction 224 the convergence demand of the user increases, or in other words, the content translates towards the vertical axis (e.g., the vertical axis 162) along a horizontal axis. Alternatively, as the graph moves from a positive value to the natural position "0," or in a negative direction 226, the divergence demand of the user increases, or in other words, the content translations away from the vertical axis along the horizontal axis. The graph 222 is only for the right side (e.g., for viewing with the right eye), and also has time for one axis verse horizontal translation movement relative to a neutral position "0." The directions 224, 226 also apply to the graph 222 with regard to convergence or divergence.

The left side of the graph 220 shows one example of a predetermined pattern of movement 228 that has a moving step 230 and a time delay interval 232. As shown, the amplitude (or the amount of horizontal translation) for each of each of the moving steps 230 is substantially the same. Similarly, the time delay interval 232 are substantially the same. A given delay step (e.g., of the delay steps 232) is the amount of time that passes with the content presented at the current location (for a particular side) to remain in the current location. So, a horizontal line on the graphs 220, 222 indicates that the content is not translating, but is rather staying in the particular location for the amount of time defined by the length of the horizontal line. Alternatively, a vertical line on the graphs 220, 222 indicates that the content will translate horizontally by the amount defined by the length of the vertical line. Arrows have been illustrated for the predetermined pattern of movement 228 of graph 220 to demonstrate how the content directionally moves with respect to time. Additionally, although the moving steps 230 are illustrated as being substantially vertical, this does not mean that the change in display happens instantaneously, but rather that such a change is imperceptible to the user's eyes (e.g., occurring faster than 0.167 seconds corresponding to 60 Hz that is imperceptible to a user's eye).

As shown in the left side of the graph 220, the predetermined pattern of movement 228 has a maximum convergence value 234. This maximum convergence value 234, generally, can be an indicator for how well a user is progressing through multiple treatment sessions, and can be an indicator for the severity of a binocular vision disorder. For example, if over time, the user is increasing the maximum convergence value 234, without any issues (e.g., double vision, discomfort, and the like), then the user's binocular vision disorder can be viewed as being improved. As another example, as a baseline test (described below), if the maximum convergence value 234 is less than a threshold value, then the doctor can diagnose the user as having a binocular vision disorder. Similarly, a user's baseline maximum convergence value 234 can be compared to multiple thresholds to determine a severity of the binocular vision disorder.

The left side of the graph 222 of FIG. 9 has the same predetermined pattern of movement 228, but for the right side of the user (e.g., for viewing with only the right eye). Thus, each of the moving steps 230 and the time delay intervals 232 are substantially the same and happen at the same (or substantially the same) point in time. Additionally, the maximum convergence value 234 for the graph 220 is the same as the maximum convergence value 234 for the graph 222.

The right side of the graphs 220, 222 show a different predetermined pattern of movement 236. In some cases, the user (e.g., via the computing device 102), or the practitioner (e.g., via the computing device 104 and instructing the computing device 104) can modify the predetermined pattern of movement, especially based on previous successful completions of past predetermined patterns of movement. As shown, the predetermined pattern of movement 236 has an increased vergence demand for the user as compared to the predetermined pattern of movement 228, where the increased vergence demand can be based on an increase in the maximum convergence value, an increase in the amplitude of the moving steps, or a decrease in the time delay intervals. The predetermined pattern of movement 236 has all of these convergence demand increases, with moving steps 238 having a greater amplitude than the moving steps 230, with time delay intervals 240 that are less than the time delay intervals 232, and with a maximum convergence value 242 that is greater than the maximum convergence value 234.

Figure 10:
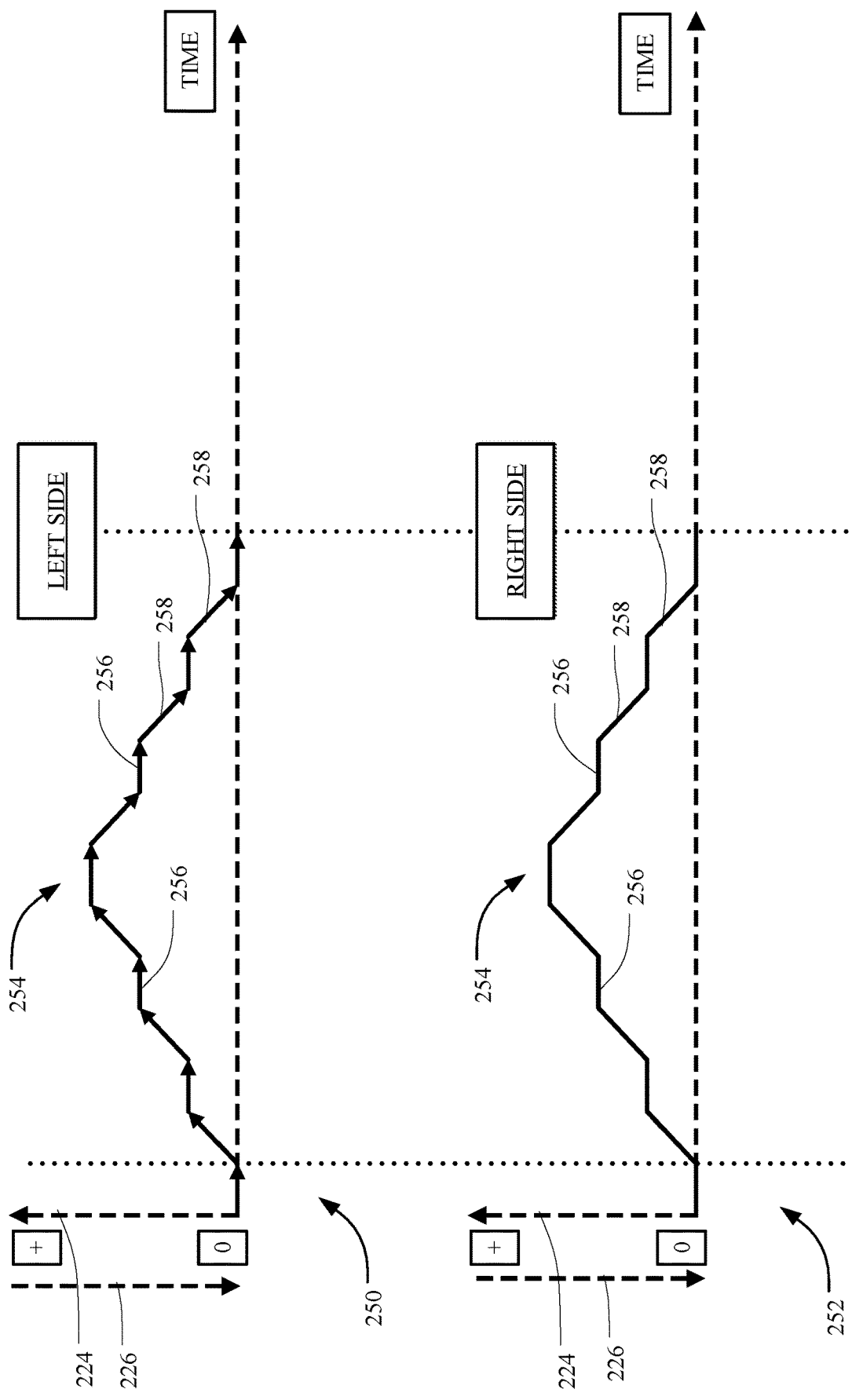
FIG. 10 shows graphs each having a predetermined pattern of movement that adjusts the vergence demand of a user in accordance with the present disclosure.

FIG. 10 shows graphs 250, 252 each having a predetermined pattern of movement 254 that adjusts the vergence demand of a user. Similarly to the graphs 220, 222, the graphs 250, 252 also have the directions 224, 226 having the similar rules (e.g., movement along direction 226 increases convergence, while movement along direction 226 decreases convergence, or increases divergence). As shown, the predetermined pattern of movement 254 also has substantially similar time delay intervals 256. However, the predetermined pattern of movement 254 has movement steps 258 that are visually perceptible to the user, which appear (to the user) as the particular content presented on a display translating at a horizontal velocity (defined by the slope of the a given movement step 258) until reaching the time delay interval 256. Similarly to the descriptions above, the content is presented for the left side of the user (e.g., only the left eye) according to the predetermined pattern of movement 254, and the content is also presented for the right side (e.g., only for the right eye) according to the predetermined pattern of movement 256.

Although the above description had substantially uniform amplitudes (or slopes) of the moving steps, and substantially uniform time delay intervals, within a given predetermined pattern of movement 228, 242, 254, in alternative non-limiting examples, the amplitudes (or slopes) of the moving steps, and the time delay intervals, within a given predetermined pattern of movement 228, 242, 254 can vary. This can be advantageous at least because this can prevent the user from predicting, or becoming acclimated, to the movement patterns, which can increase the focus of the user.

In some non-limiting examples, the predetermined patterns of movement can be determined based on various criteria, or parameters. For example, in some cases, the amplitude of the moving step can be determined based on the following equation (1):

$$\text{Moving Step} = \text{ScreenDistance} * \tan(\text{Vengence Step}/1.75)/2 \qquad (1)$$

With regard to equation (1), the moving step (as described above) is the distance each content presented on the display horizontally shifts (or translates), the ScreenDistance is the distance from the display to a lens (e.g., if the display is projected through a lens to the user), and the Vergence Step is the amplitude of the vergence change each time (e.g., each time the display translates). In some non-limiting examples, the vergence step can be a default value of 2.0 prism diopter. In some non-limiting examples, the amplitude of the moving step can depend on the Viewing distance (e.g., the distance between the eyes and the display), the magnification of a lens that is located between the display and the user (if the system includes a lens), and the Vergence step.

Additional parameters (or criteria) can be used to determine the predetermined pattern of movement. For example, the inter-pupil distance can be used to determine the initial locations of the content, which is the neutral position (or location), indicated as "0" in FIGS. 9 and 10. In particular, the horizontal distance between the central locations (e.g., centroids) of each of the portions of content (e.g., the portions of content 156, 158) can be identical (or substantially similar) to the inter-pupil distance of the user, with the vertical axis that bisects the display (or other vertical axis) intersecting the horizontal distance. In some non-limiting examples, the inter-pupil distance can be defaulted to 60 mm.

In some non-limiting examples, the distances above (in millimeters) should be converted to a pixel length that is related to the particular display, so that the computing device 102 (or other suitable computing device) can cause appropriate functioning of the display that is in communication with the computing device 102. In other words, the distances above in millimeters can be converted to pixel lengths that correspond to the particular display device, which can consider the pixel density (e.g., the individual pixel dimensions using a readily obtainable value). The equation (2) below can be used to convert the distances in millimeters to pixel lengths, while the equation (3) below can be used to convert the distances in pixel lengths to millimeters.

$$\text{pixels} = \text{mm} * xdpi * (1.0/25.4) \qquad (2)$$

$$\text{mm} = \text{pixels}/(xdpi * 25.4) \qquad (3)$$

In equations (2) and (3), xdpi is the pixel density for the display in communication with the computing device 102. With regard to equation (3), px is the prism power, such as for the magnification of the lens(es), which should be converted into millimeters.

Figure 11:
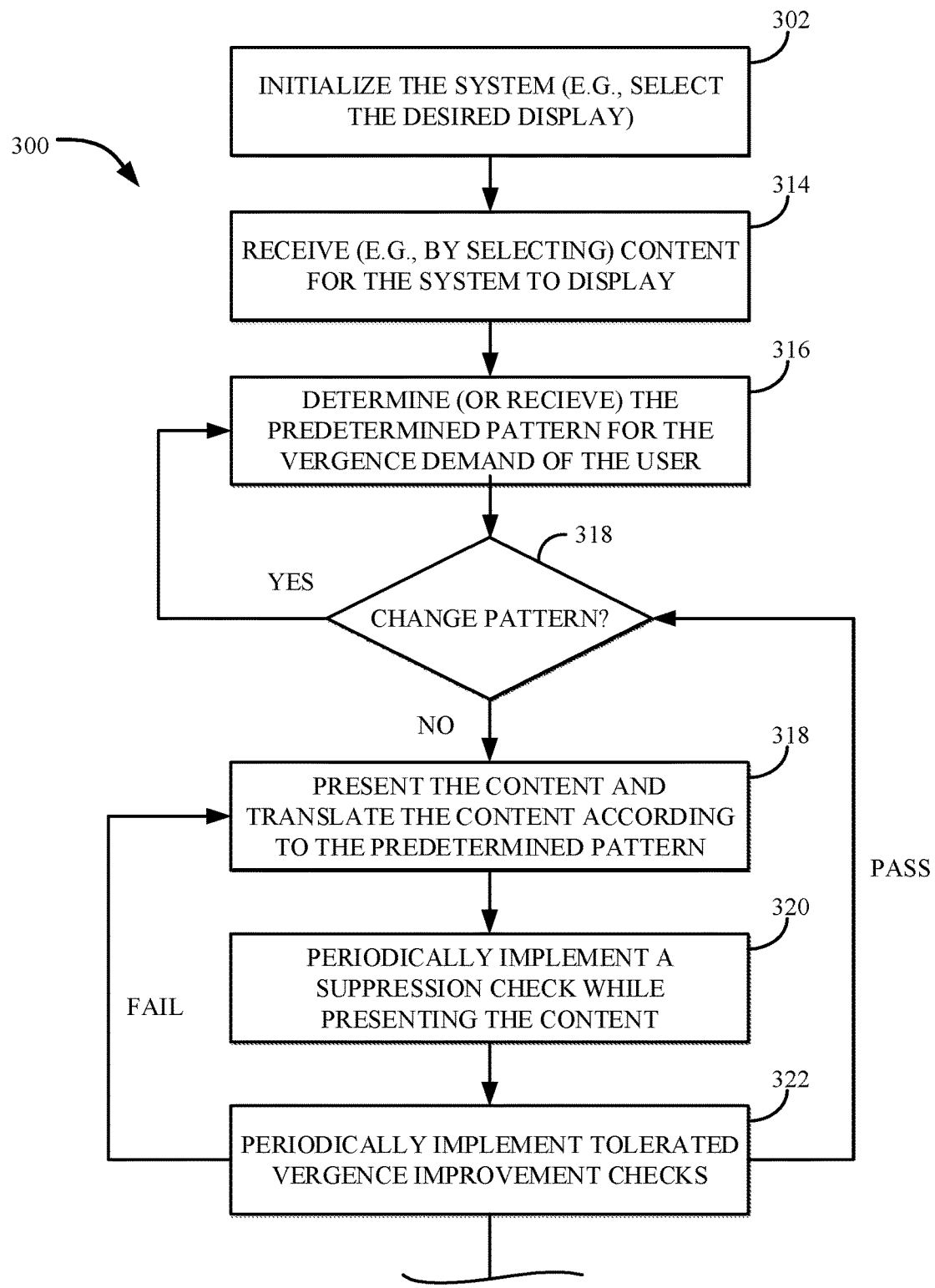
FIG. 11 shows a portion of a flowchart of a process for treating a binocular vision disorder in accordance with the present disclosure.
Figure 12:
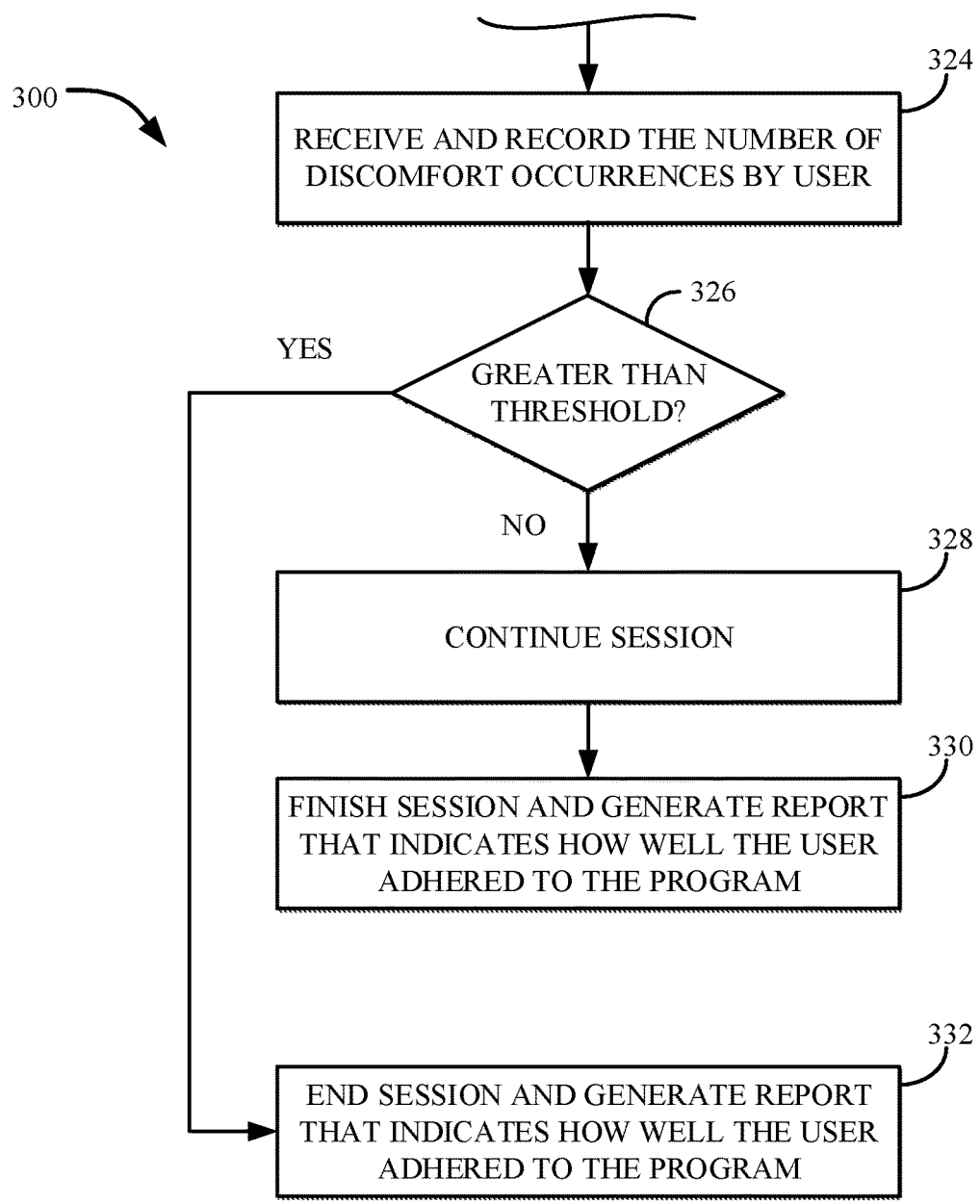
FIG. 12 shows the remaining portion of the flowchart of the process for treating a binocular vision disorder.

FIG. 11 shows a flowchart of a process 300 for treating a binocular vision disorder. In some non-limiting examples, appropriate steps within process 300 can be implemented using a suitable computing device (e.g., the processor of the computing device 102). At 302, process 300 includes initializing the system. In some non-limiting examples, the user selects the desired display device and establishes the appropriate communication between the computing device (e.g., the computing device 102) and another computing device (e.g., the computing device 104, the server 106, or both). In some non-limiting examples, the user couples and secures the display (and the computing device, such as a smartphone) to a head mounting device. In other non-limiting examples, the user secures the virtual reality headset (or other head mounting structure, such as smart glasses) appropriately.

Figure 13:
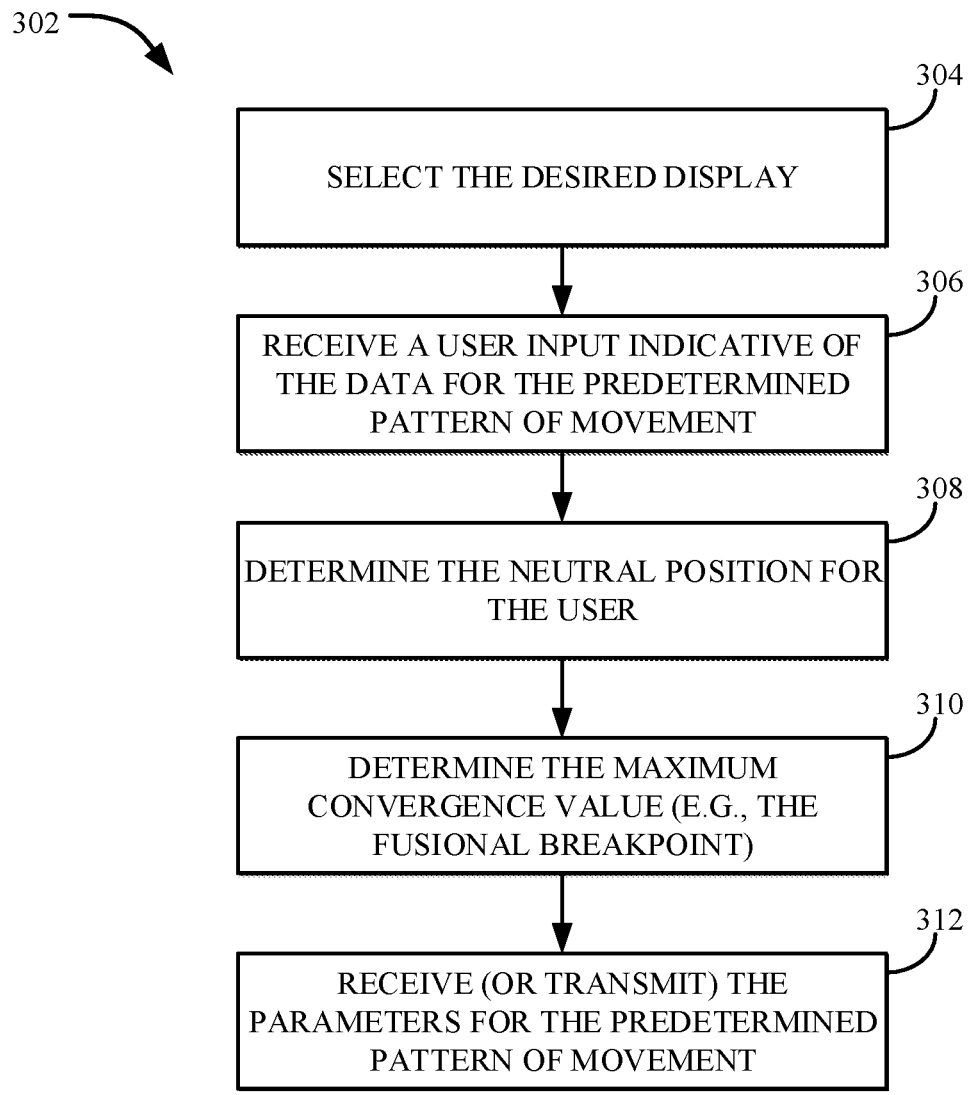
FIG. 13 shows a flowchart of a sub process of the process of FIGS. 11 and 12 for initializing the system(s).

FIG. 13 shows a flowchart of a sub process 302 of the process 300 for initializing the system(s). At 304, sub process 302 can include selecting the desired display, and securing the display, if needed, to the user (and establishing appropriate communication paths as needed). Additionally, this can include establishing communication between the controller device (if used, such as the controller device 132) and the computing device.

At 306, sub process 302 can include receiving a user input indicative of data for the predetermined pattern of movement. The user input can include any parameters related to the predetermined pattern of movement, such as, for example, the Moving Step, the Screen Distance, the Vergence Step, the inter-pupil distance, the Viewing Distance, the magnification (e.g., of a lens of the head mounted device having the display), the pixel density of the display, a desired total treatment length, amount and time length of predetermined breaks, and the like. In some non-limiting examples, the user can simply interact with the display presenting a menu (or other graphical user interface) to select the type of display the user is using (or product of the computing device, such as a specific brand and model of a computing device, such as a smartphone), which can automatically be tied to any or all of the parameters related to the predetermined pattern of movement. Thus, the user input being indicative of the type or model of the display, when received by the computing device (or another computing device, such as the server), can automatically populate (e.g., from a database, or other data or look-up table) the parameters related to the predetermined pattern of movement.

At 308, sub process 302 can include determining the neutral portion for the user. In some cases, as described above, the neutral position (e.g., the starting locations of the content presented on one or both of the displays), can be set based on the inter-pupil distance, which can be received by the computing device from the user input, converted to appropriate units (e.g., with the pixel density calculation), and used to set the starting horizontal distance for the user. In some cases, the computing device can implement a procedure for determining the neutral position for the user. In this procedure, portions of content (e.g., calibration images) can be presented at the farthest location on the display(s) (or another location), such that the horizontal distance between the first portion of content and the vertical axis (that bisects the display) is large, and the horizontal distance between the second portion of content and the vertical axis is large. The portions of content are then translated horizontally toward the vertical axis according to a predetermined pattern of movement (e.g., a calibration predetermined pattern of movement, that includes the videos horizontally translating the same amount each iteration) until the user determines that the portions of content are at a comfortable, and relatively straight orientation, which at this point in time, the user transmits a user input (e.g., by a head nod in the case of the virtual reality headset, or by actuating a button on the controller device) to, and which is received by, the computing device. This user input indicative of a comfortable location can allow the computing device to determine the locations of content presented on the display(s) that correspond to when the user input was received (e.g., the last locations). In other cases, the user can interact with a user interface to selectively adjust the locations of the portions of content, such as with a slider, or wheel on a graphical user interface. Then, once the desired position is selected, the user can select (on a graphical user interface) to lock in the position, which can then transmit the user input to be received by the computing device, which is indicative of the neutral position of the location of the portions of content presented on the display(s).

At 310, sub process 302 can include determining the maximum convergence value (e.g., the fusional breakpoint) for the user. In some non-limiting examples, the computing device presents the portions of the content (e.g., the video) to the user with a vergence demand corresponding to an object at infinity (e.g., a distance larger than 6 meters or 20 feet). In some cases, this is the neutral position (or location) that the portions of content are presented on the display(s). Then, progressively, the videos are shifted horizontally towards the center of the screen with a predefined speed and predefined moving steps that can be chosen by the prescribing doctor (e.g., via the computing device 104). The user is asked to report when experiencing double vision with a user input (e.g., a nod of the head for the virtual reality headset, an actuation of a button on the controller device, and the like). Once the computing device receives this user input, the computing device records and calculates this point (location, distance, and the like) as the user's fusional breakpoint (e.g., the onset of double vision), which is the maximum convergence value for each of the portions of content (e.g., the maximum convergence value 234). Determining the maximum convergence value (or the fusional breakpoint) of the user can effectively calibrate the predetermined pattern of movement (or can be used to create the predetermined pattern of movement). In some cases, after determining and reporting the fusional breakpoint, the computing device will then reduce progressively the vergence demand down to "0" (e.g., the neutral point) using the same speed and moving steps. Generally, a high vergence demand corresponds to a pair of images close together on the display, which simulates an extremely near target in the real life. Starting again from the neutral position "0" that simulates objects at infinity, the computing device progressively increases the vergence demand (e.g., horizontally translating the portions of content on the display towards the vertical axis) until the user reports again double vision (e.g., by another user input). This sequence can be repeated three (or more or less) times during the binocular fusion testing protocol at the beginning of the therapy, which can create an average maximum convergence value for the user. As described above, this maximum convergence value for the user can be utilized to generate the predetermined pattern of movement for the current session, can be reported, saved, and compared (e.g., to compare to the user's historical measurements, baseline measurements, and the like, to determine patient progress).

At 312, sub process 300 can include receiving (or transmitting) the parameters for the predetermined pattern of movement. In some cases, the computing device of the user receives all of the parameters and generates the predetermined pattern of movement. Thus, the computing device does not necessarily need to transmit the parameters for the predetermined pattern of movement to another computing device. In other cases, the server (or the computing device of the practitioner) is the device the generates the predetermined pattern of movement, and thus the computing device of the user can transmit these parameters to the server (or other computing device).

At 314, process 300 can include receiving content for the computing device to present on the display. In some non-limiting examples, the computing device can receive at least three different kinds of video input: personal videos stored in on memory of the computing device, videos (or other content) screencast from a second computing device (e.g., a second mobile device) through a Wi-Fi connection, and videos (or other content) streaming from internet sources. In some cases, the content (e.g., videos, books, magazines, and the like), which can be selected by a user interacting with a user interface in communication with the computing device, and retrieved from memory stored on the computing device. In other cases, the content can be screen-casted, by a user navigating to a middle tab of a menu (e.g., a graphical user interface) that illustrates a screencast option. This modality can require the presence of a second computing device running the same software and being connected with the same Wi-Fi network as the computing device of the user. After the "Share" option has been selected (by the second computing device), any content on the screen of the second device (or other application) will be transmitted to and received by the computing device of the user. Once the "Receive" option is selected on by the second computing device and received by the first computing device, the computing device will present on the display, the content that has been screencast. In some cases, if no device (e.g., the second computing device) is found under the same Wi-Fi network, the screencast operation displayed on the computing device of the user will become unavailable and the controls will be grayed out. As described above, the content can be anything including, but not limited to documents, webpages, camera feeds, videogames, other games, e-books, and the like.

Generally, because the user controlling the screen-casting device (e.g., the first computing device) is not able to see the display of the device being casted (e.g., the second computing device), a finger tracking mode (e.g., if the first computing device has a touchscreen) or other cursor tracking mode can be enabled on the first computing device to allow the user to interact, via the first computing device, with the second device this is generating the video source. In some cases, if the content to be screen casted is a videogame, the user selected game will run on the device in the hands of the user (e.g., the second device) and only the video will be projected to the first device (e.g., the device mounted in the headset). This way, controls to allow the user to play the game reside in the second device as well as the audio source for the game.

In some non-limiting examples, the computing device can stream content from a suitable communication network. For example, the user can select, via a user input received by the first computing device, an operation mode of streaming content from the internet (or other communication network) that allows the user to visualize content (e.g., a video) chosen from third party providers (e.g. media, television providers, and the like), software, or other webpages on the internet to be presented on the display for the treatment session (e.g., for the predetermined pattern of movement). In some non-limiting examples, the computing device includes algorithms and media protocols to allow for streaming from servers using Digital Living Network Alliance ("DLNA") protocols which is used by providers in the U.S. including Apple TV, and AirPlay, Discovery and Launch ("DIAL") protocols which is used by providers such as Netflix, and Web Real-Time Communication ("WebRTC") protocols (or other appropriate protocols).

In some non-limiting examples, the user, via the computing device, can navigate online video contents, and can select the option of projecting the selected video to the vision therapy software (e.g., via a user input on the computing device). In some non-limiting examples, when the computing device presents, on the display, the content according to the predetermined pattern of movement, the computing device can also present the same playback controls that can include a pause button, a play button, a fast-forward button, and a rewind button (see e.g., the main tab of FIG. 20). In some non-limiting examples, this streaming option can be extended to personal computers (e.g., the second computing device) running a web browser. In this case, the computing device running the vision therapy software can be automatically recognized as an external video projector for which the video or internet tab on the personal computer can be sent from (and received by the first computing device), if both computing devices are connected to the same Wi-Fi network.

At 316, process 300 can include determining (or receiving) the predetermined pattern of movement for adjusting the vergence demand of the user. In some cases, the computing device (of the user) can generate the predetermined pattern of movement by using the parameters previously received or otherwise determined, such as, the Moving Step, the Screen Distance, the Vergence Step, the inter-pupil distance, the Viewing Distance, the magnification of a lens of a head mounted device (or glasses), the pixel density of the display, the total treatment length, and the amount (and time lengths) of predetermined breaks. In other cases, the server (or computing device of the practitioner) can transmit the predetermined pattern of movement to the first computing device, for example, after being modified by the practitioner (e.g., via the second computing device). In other cases, the second computing device can transmit modified parameters that can override the previously received parameters for the predetermined pattern of movement, such that the practitioner (via the second computing device) can prescribe a unique treatment regimen for the user.

At 318, process 300 determines whether or not to change the predetermined pattern of movement. If, for example, the process 300 has just determined the predetermined pattern of movement, the process 300 can determine that the process 300 can proceed to 320 of process 300. Alternatively, if the process 300 has determined that the predetermined pattern of movement should be changed (e.g., after receiving an indication that the user has passes a periodic vergence improvement check) the process 300 can modify the predetermined pattern of movement, and proceed back to 316 of process 300.

At 318, process 300 includes presenting the content (e.g., received at 314 of process 300) to the display(s) and translating the content according to the predetermined pattern of movement. In some non-limiting examples, as described above, the content received at 314 of process 300 is duplicated and presented on the display (or the displays) with one portion of content being presented on one side of the display (or one display) and another portion of content being presented on another side of the display (or the other display), such that each of the portions of content are derived from the content receive at 314 of process 300.

At 320, process 300 includes periodically implementing a suppression mask, while presenting the content according to the predetermined pattern of movement. Generally, in cases of visual discomfort (e.g., with double vision), the human brain is able to suppress the view from one eye in order to remove the double vision. Since binocular vision therapy is making use of the patients vergence limits, it is possible that during a maximum vergence demand condition the patient suppresses one of the two images. For this reason, a suppression check protocol can occasionally obscure the middle part of the image (or portion of content) to disrupt any suppression that may be occurring. Since we are not aware of the suppressing eye, the obscuration of the middle part of the image (or content) can alternate between the left and right images (or portions of content) three (or more of less) times to disrupt any suppression mechanism. This protocol can be repeated at regular time intervals that can be selected from the settings or from the prescription file. In some non-limiting examples, the occurrences of the suppression check protocol can be randomized, which can help to maintain the user's focus.

In some non-limiting examples, the suppression protocol can have the suppression mask always present to one eye (e.g. the good eye in patients with amblyopia). In this case the central vision of the good eye can be suppressed and the lazy eye is forced to use in the treatment. However, as the peripheral vision of the masked eye can still see a portion of the image, binocular fusion may be maintained to a certain level during the treatment.

In some non-limiting examples, the computing device can also allow for the activation of dichoptic red marks at the center of the two portions of content, to monitor the user perception (e.g., via a web browser). These marks can appear at regular, or random intervals during the treatment session, or can be initiated by a practitioner (e.g., via the second computing device). The shapes of the red marks can vary, but generally, the user ideally should only be able to view the dichoptic red marks as a single image. In other words, if the user is properly fusing the images (e.g., the two portions of content) and is not suppressing, he/she should be able to perceive the central object binocularly as a single image with no occlusions indicating that no suppression mechanism from the brain is activated (and verifying that the user is still able to fuse the images). In some cases, as soon as the user perceives a disrupted central image (e.g., double vision or blurry partial fusing of the dichoptic red marks), he/she can be asked to transmit a user input (e.g., by a head gesture, such as a nod) to be received by the computing device.

Figure 14:
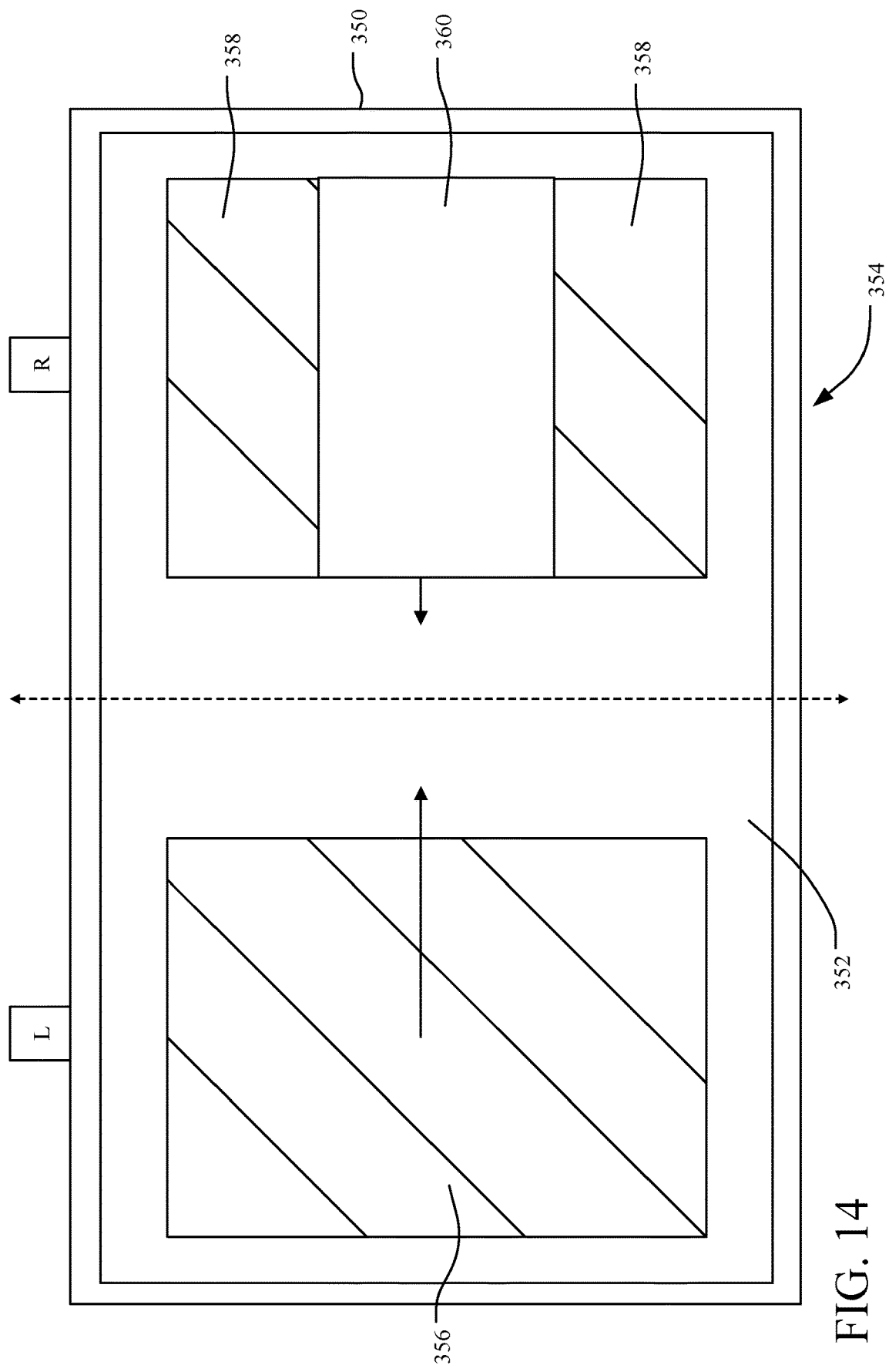
FIG. 14 shows an illustration of a display having a display surface that is presenting a dichoptic presentation to the user that defines a suppression mask.

FIG. 14 shows an illustration of a display 350 having a display surface 352 that is presenting a dichoptic presentation 354 to the user that defines a suppression mask. As shown, the dichoptic presentation 354 has a first portion of content 356 presented on the left side of the display 350, and a second portion of content 358 presented on the right side of the display 350. The second portion of content 358 has an occluded region 360 that is optically similar (e.g., the same color, such as black) to the region of the display surface 352 that are not presenting the first or second portions of content 356, 358, such that the occluded region 360 effectively "cuts-off" the second portion of content 358. The occluded region 360 is centrally located and horizontally bisects the second portion of content 358, however, in other non-limiting examples, the occluded region 360 can be centrally located to vertically bisect the second portion of content 358. As described above, the occluded region 360 can be alternated, so that the occluded region 360 is presented on the first portion of content 356 (but not on the second portion of content 358). Additionally, the location that the occluded region 360 appears on can be alternated. Generally, the occluded region 360 only appears on either the first portion of content 356 or the second portion of content 358, but not both. In some non-limiting examples, the size or location (or both) of the occluded region 360 can be iteratively adjusted. In some non-limiting examples, the occluded region 360 can be presented for a period of time.

Figure 15:
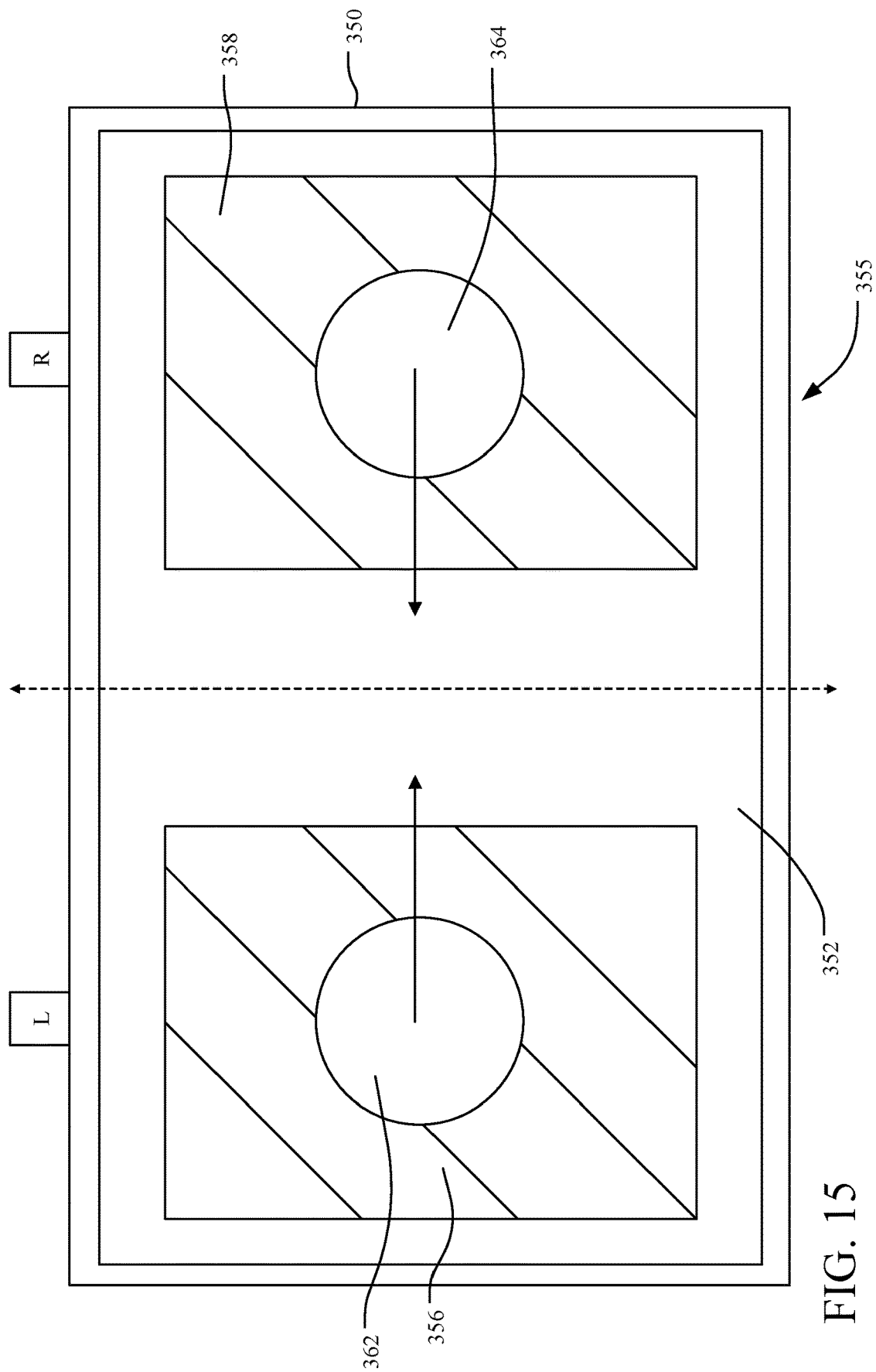
FIG. 15 shows an illustration of the display of FIG. 14 having the display surface that is presenting another dichoptic presentation to the user having a dichoptic activation.

FIG. 15 shows an illustration of the display 350 having the display surface 352 that is presenting a dichoptic presentation 355 to the user having a dichoptic activation. As shown, the dichoptic presentation 355 has the first portion of content 356 presented on the left side of the display 350 and the second portion of content 358 presented on the right side of the display 350. The dichoptic presentation 355 also includes a first dichoptic mark 362 superimposed on a central region (e.g., the centroid) of the first portion of content 356 and a second dichoptic mark 364 superimposed on central region (e.g., the centroid) of the second portion of content 358. When the dichoptic presentation 355 is presented to the user, ideally the user should merge the images together to easily view the contour, shape, features, and the like, of a single dichoptic mark from the merging of the first and second dichoptic marks 362, 364. However, as described above, if this doesn't happen, the user can indicate, via a user input received by the computing device, that the user has a disrupted view of the merged single dichoptic mark. The dichoptic marks 362, 364 are substantially similar (or identical), each having a similar shape, color, and the like. Although, the dichoptic marks 362, 364 are illustrated as being (red) circles, in other non-limiting examples other shapes, and colors are contemplated. As shown, the first dichoptic mark 362 is retained within the first portion of content 356, while the second dichoptic mark 364 is retained within the second portion of content 358.

At 322, process 300 can include periodically implementing a tolerated vergence improvement check. In some non-limiting examples, the computing device can periodically check for improvements of the patient's tolerated vergence demand. For example, three specific therapy statuses can be automatically alternated in the system to determine the patient's tolerated vergence demand, which can include a) a maximum effort period when the user is required to move the eyes from the neutral point to maximum defined vergence demand, b) a minimal effort period when the user is required to move the eyes from the neutral point to a middle vergence demand that can be easily tolerated, and c) a monitoring period when the user is pushed beyond the recorded maximum vergence demand to check any improvement in the fusional breakpoint. In some cases, for example, if in status c) the new vergence demand tolerated is greater than the one previously recorded, a new progress is registered and the therapy protocol is adjusted to the new achievement. For example, if at 322, process 300 determines that the user has failed the maximum vergence effort periodic treatment check (e.g., indicated by a user input indicating discomfort, or double vision that is received by the computing device), the computing device will proceed back to 318 of process 300 and present the content according to the predetermined pattern of movement. If, however, at 322 process 300 determines that the user has passed the maximum vergence effort periodic treatment check (e.g., by the lack of a user input indicating discomfort, not received by the computing device), process 300 can proceed back to 318 of process 300 to adjust the predetermined pattern of movement to make the vergence demand for the user more difficult (e.g., increasing the individual movement steps, or the maximum convergence value of the predetermined pattern of movement).

Figure 16:
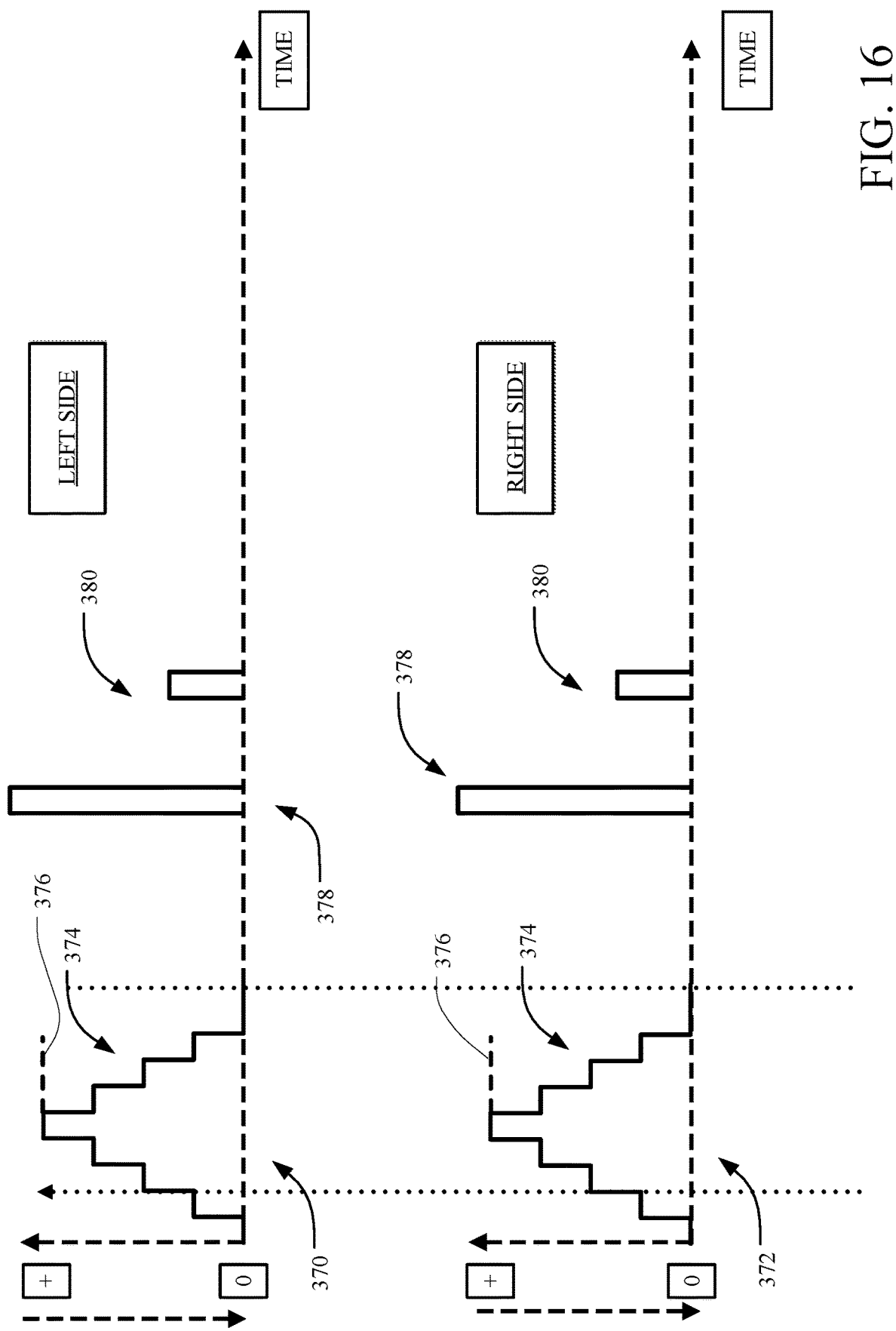
FIG. 16 shows graphs of predetermined patterns of movement for both sides of a display that adjusts the vergence demand of the user with a maximum effort period and a maximum effort period.

FIG. 16 shows graphs 370, 372 of predetermined patterns of movement 374 for both sides of a display (e.g., the left and the right sides) that adjusts the vergence demand of the user, with a maximum effort period and a maximum effort period. The graphs 370, 372 are interpreted the same as the previously described graphs (e.g., graphs 220, 222), with movement away from the neutral position "0" increasing the convergence demand, and movement towards the neutral position "0" decreasing the convergence demand (or increasing the divergence demand). As shown, the patterns of movement 374 have a maximum convergence value 376. As described above, periodically the computing device can implement a maximum effort vergence demand 378 that has a convergence value that exceeds the maximum convergence value 376 of the predetermined pattern of movement 374. Additionally, and periodically, the computing device can implement a minimal effort vergence demand that has a convergence value between the neutral position "0" and less than the maximum convergence value 376. In some cases, the convergence value of the minimal effort convergence demand is less than 50% of the maximum convergence value 376.

At 324, process 300 can include receiving and recording the number of discomfort occurrences by the user. Each occurrence can be transmitted by a user input (e.g., as previously described) and received by the computing device. In some cases, when the computing device determines that a user has experienced discomfort (e.g., by receiving a user input), the computing device can, for a temporary period of time during the session, decrease the maximum convergence value for the user (e.g., by the threshold amount, such as 10%). Additionally, subsequent user inputs indicative of discomfort (e.g., breaks) can further decrease the maximum convergence value for the user (e.g., by the threshold amount). At 326, process 300 can determine if the number of discomfort occurrences is greater than a threshold value (e.g., four times) during a session. If at 326 process 300 determines that the number of discomfort occurrences is greater than the threshold value, process 300 can proceed to 332 of process 300 to end the session and generate the report that indicates how well the user adhered to the program. For example, all of the data that had been recorded during the session, including how many instances of discomfort, when the instances of discomfort occurred with respect to the predetermined pattern of movement, the outcome of any of the periodic tests, and the like, can be compiled, analyzed, and the like to generate the report. Alternatively, if at 326 process 300 determines that the number of discomfort occurrences is less than a threshold value, process 300 can proceed to 328 of process 300 to continue the session. In some non-limiting examples, if a user input received by the computing device indicative of a break (e.g., from the user actuating a "break" button on the controller device), process can pause the session for the amount of time indicated by a break, and after the break is finished, the session can readily continue.

At 330, process 300 can include finishing the session, and generating a report that indicates how well the user adhered to the program, similarly to the report at 332 of process 300. In some non-limiting examples, the computing device (or the practitioner's computing device) can generate a historical report from the currently received session data, and the data of historical sessions, to determine how well the user is progressing.

Figure 17:
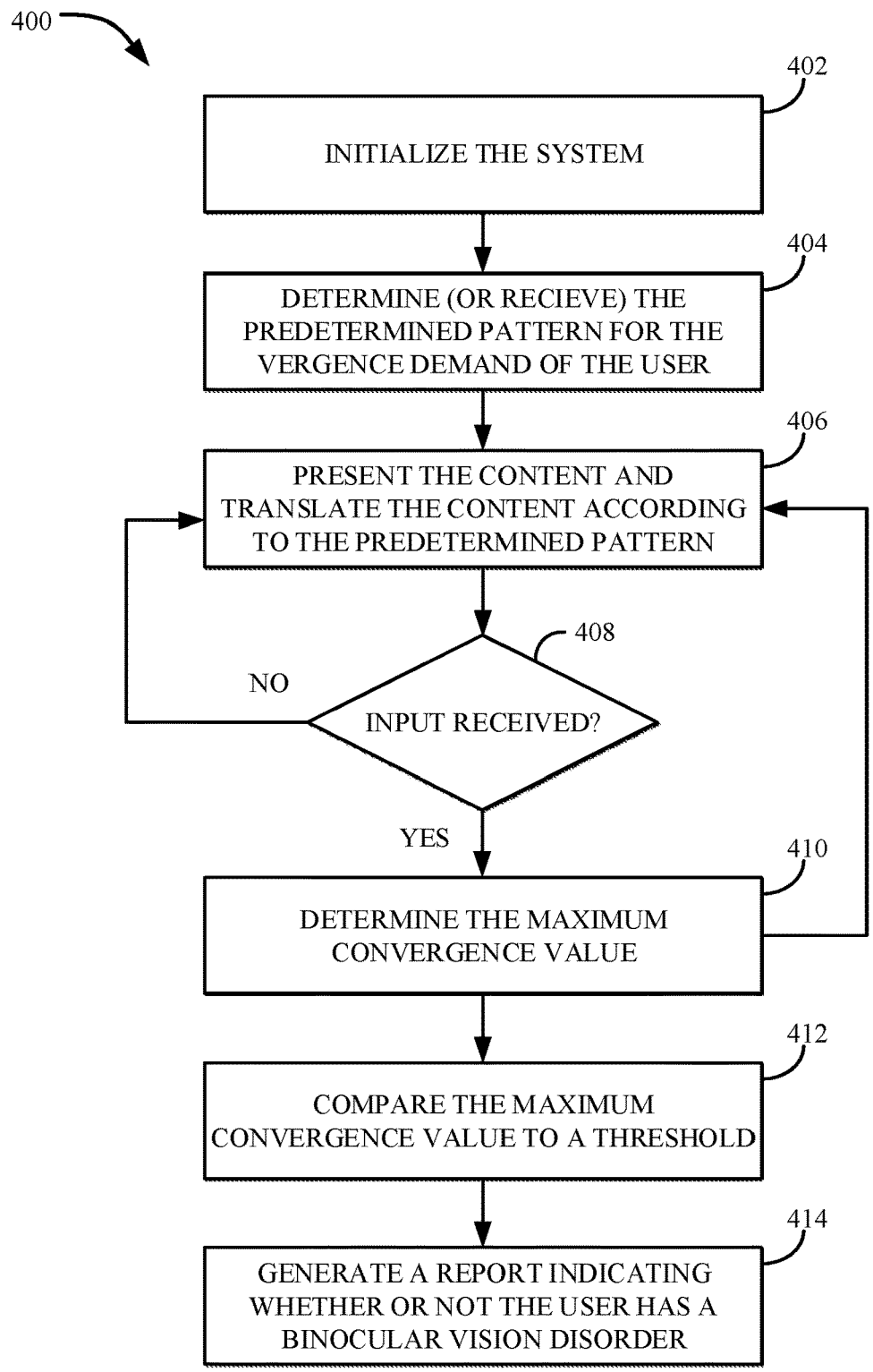
FIG. 17 shows a process for evaluating a presence or severity of a binocular vision disorder of a user.

FIG. 17 shows a process 400 for evaluating a presence or severity of a binocular vision disorder of a user. Process 400 can be implemented with the computing device (e.g., the computing device 102), or other suitable computing device, as appropriate. At 402, process 400 includes initializing the system(s), which can be similar to initializing the system at 302 of process 300. At 404, process 400 includes determining or receiving the predetermined pattern of movement for the vergence demand of the user, which again, can be similar to 314 of process 300. At 406, process 400 can include presenting the content and translating the content according to the predetermined pattern of movement (e.g., determined at 404 of process 400). In some non-limiting examples, the predetermined pattern of movement at 404 of process 400 can be a standard movement pattern, such as one that a person without binocular vision issues (or disorders) could readily complete.

At 408, process 400 determines if a user input (e.g., from a user) has been received, which is indicative of (significant) discomfort, blurry images, or double vision for the user. If at 408, process 400 determines that no user input has been received, process 400 proceeds back to 406. Alternatively, if at 408 process 400 determines that a user input has been received, process 400 can proceed to 410.

At 410, process 400 includes determining a maximum convergence value, based on the user input and the location on the predetermined pattern of movement when the user input was received. Once the maximum convergence value 410 has been determined (or at a different point), process 400 can proceed again to complete steps 406, 408 starting at the beginning of the predetermined pattern of movement (e.g., the neutral location). This way, additional maximum convergence values can be utilized (each from a different trial) to generate an average convergence value for the user.

At 412, process 400 includes comparing the maximum convergence value (or average convergence value) to a threshold value. In some cases, if the convergence value is less than a threshold value, the computing device can indicate that the user has (or is likely to have) a binocular vision disorder. In some cases, the convergence value can be compared to multiple thresholds to determine a severity of a binocular vision disorder.

At 414, process 400 includes generating a report indicating whether or not the user has (or is likely to have) a binocular disorder, and if so, the severity of the binocular vision disorder. In some cases, the report can include the data collected, and comparisons to the threshold value(s).

EXAMPLES

The following examples have been presented in order to further illustrate aspects of the disclosure, and are not meant to limit the scope of the disclosure in any way.

Some non-limiting examples of the disclosure provide a head-mounted system for allowing a doctor to treat and assess binocular vision remotely. Some non-limiting examples of the disclosure aim to provide a more acceptable, accessible and attractive treatment for patients who have binocular vision disorders such as convergence insufficiency or amblyopia, and at the same time a convenient way for eye doctors to monitor and prescribe such treatment at distance. The system includes a head-mounted system with at least one processor and a display in which patients can watch videos of their choice. The system can process the selected video to provide vision exercises prescribed by physicians remotely.

Some non-limiting examples are provided to facilitate home-based visual therapy ("VT") compliance with a smartphone or other display incorporated into a head mounted display ("HMO") platform by enabling the use of a variety of video content that patients can choose (such as games, movies, and the like) as a stimulus for VT. Some existing VT tasks or dedicated VT games tend to be repetitive and unattractive, and can easily lose a patient's (child or adult) interest quickly. It is proposed that if VT can be performed while engaging in leisure activities (e.g. watching a newly released movie or playing a favorite video game), it is anticipated that the compliance and duration (dose) of VT will be greatly enhanced. Because of the greater patient engagement, it can then be possible to make in-home therapies even more effective than current in-office approaches.

In some cases, mobile platform (smartphone or smart glasses) based proposals can capitalize on the telemedicine benefits made possible by automated, self-administrated binocular vision assessment and by VT run-time data collection. Such data from in-home training sessions could help individual clinicians monitor therapy progress and provide personalized medical guidance to VT patients. This capability could in turn lower the number and improve the efficiency of office visits, reducing the overall cost of vision therapy. Furthermore, clinical researchers could analyze the data derived from multiple, de-identified VT patients to generate recommendations for improved VT protocols.

The smartphone-HMO based VT system (or other systems according to non-limiting examples of this disclosure) could trigger a paradigm shift in access and effectiveness of the assessment and treatment of binocular vision disorders, making it possible to deliver much-needed treatment to under-served and economically constrained patient populations. Currently, low cost virtual reality ("VR") goggles that turn smartphones into dichoptic HMOs are widely available. The smartphone VR goggles have become popular consumer devices and are relatively inexpensive.

The display of the images or videos in the head mounted mobile device is arranged with two views of the same video (or substantially the same video) aligned horizontally in a landscape screen, which plays the two videos simultaneously. In addition, by masking a designed portion of the screen in one of the two videos, the system can be used to treat patients with amblyopia. To initiate vision therapy, the user slides the smartphone into a virtual reality ("VR") head-mounted display (headset). Using simple head gestures, the user is able to select any of the personal video files stored in the phone by selecting the corresponding icon from the menu tab. An alternative Bluetooth controller can be used to navigate the user interface. Once the video is selected, the software begins the playback of the content in a dichoptic view (see FIG. 19) and the doctor-prescribed therapy protocol can commence.

Figure 19:
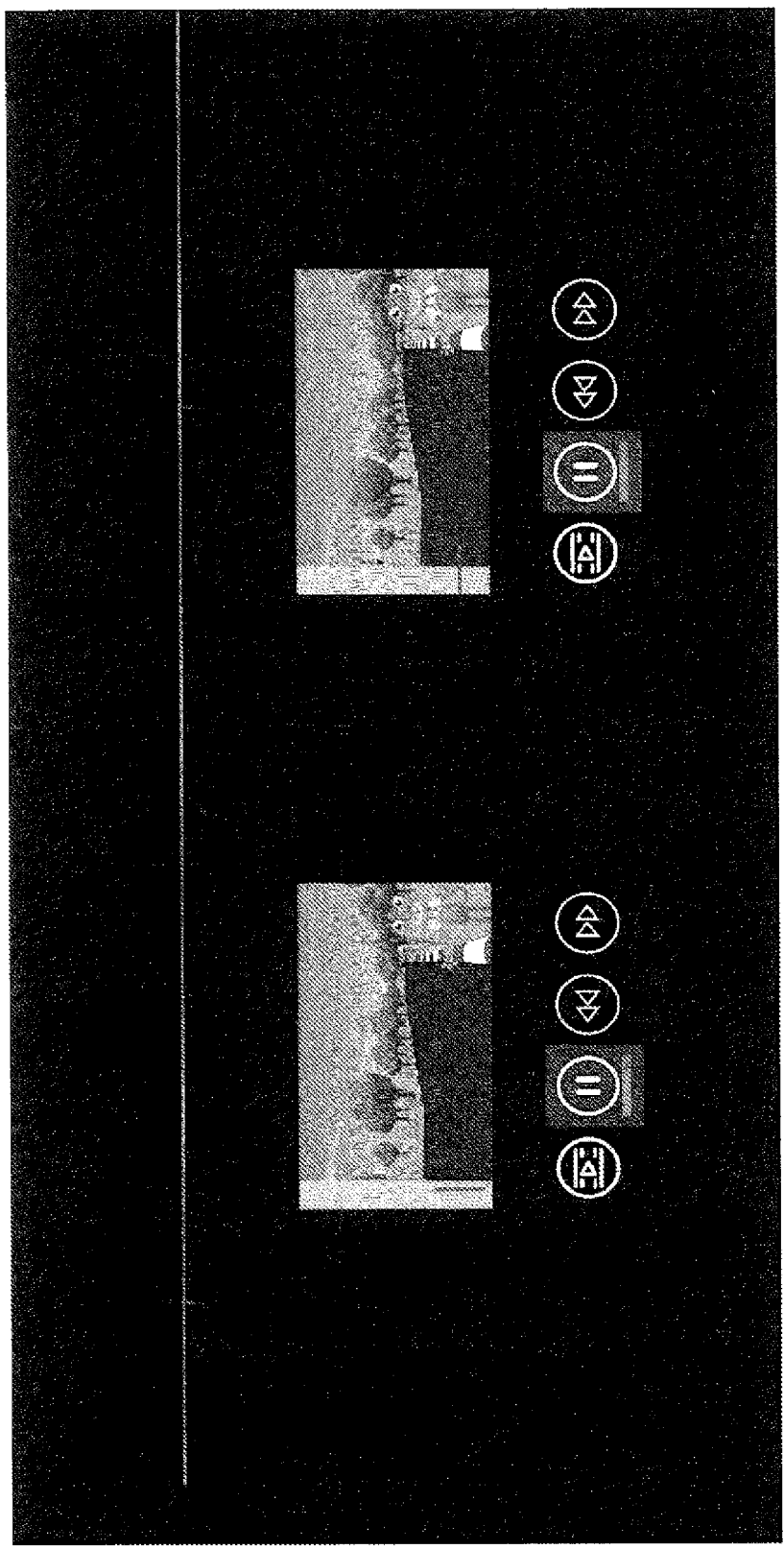
FIG. 19 shows a dichoptic presentation of a playback of user selected video during the therapy mode.

The parameters for each day of therapy are established based on the patient's responses during fusion breakpoint testing and on the doctor's prescription. At the completion of testing, the software automatically implements the therapy protocol while playing the user-selected video content. FIG. 19 shows the user interface and the dichoptic view as it appears on a smartphone screen during therapy. The user sees two images separately by the left and the right eyes and is required to follow the movement in order to perceive a single image. While in a VR headset environment, the patient cannot perform a tap gesture on the screen. User control of different playback options are accomplished by the user head gestures. Tilting the head up allows to view and select from a simple menu (playlist, play/pause, rewind 5 sec, or fast forward 5 sec). Navigation through the menu option is done via a head rotation (highlight of the desired choice) and the selection of the highlighted option is done by keeping the head in the same position for a predefined number of seconds. A loading bar is presented to help the user understand how much time is needed to select the option (FIG. 19).

Thus, the computing devices described above may include a smartphone HMO system that can employ game, video, or other stimuli for vision therapy. A computer or mobile device screen will be wirelessly connected to the smartphone HMO, and generate a dichoptic view. Users can control the content to be viewed with a Bluetooth remote (the remote is available together with some VR goggles, otherwise can be purchased separately for a few dollars), head gestures, or another hand-held mobile device that is also screen-casting the video.

Figure 18:
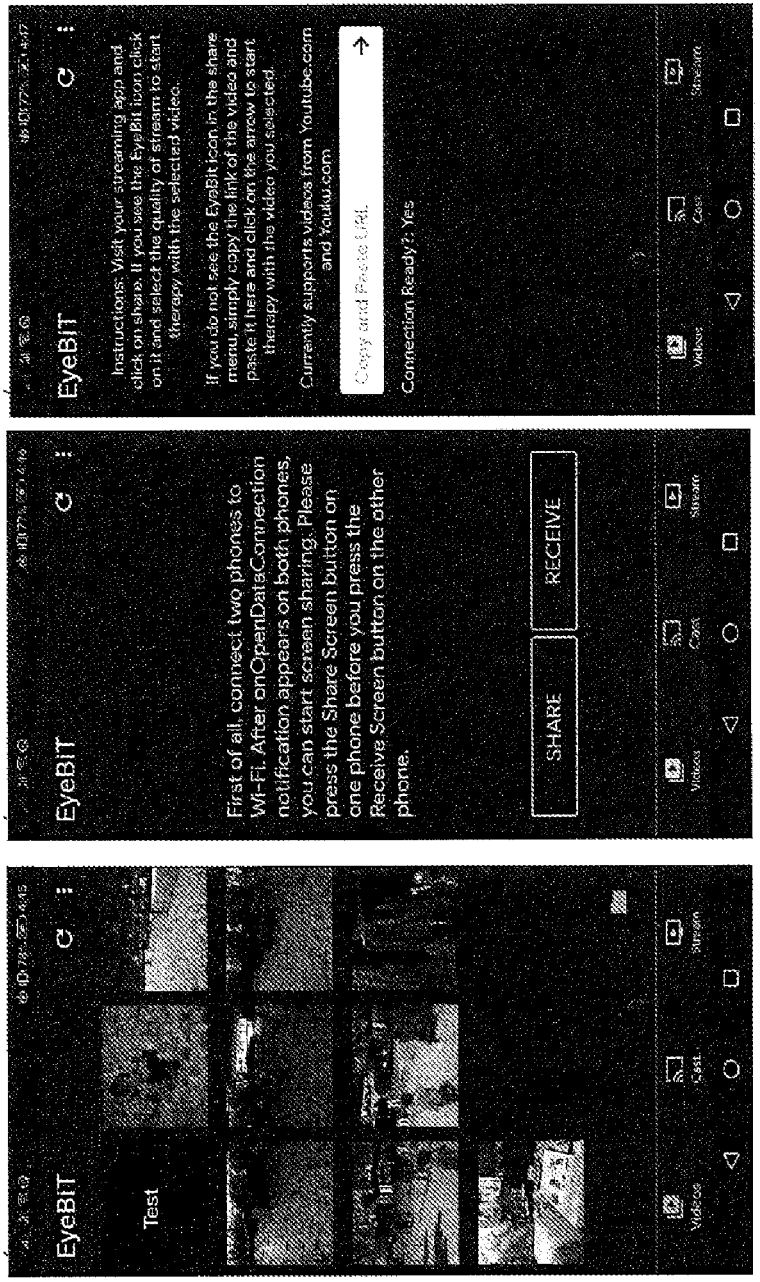
FIG. 18 shows the available tabs of the prototype in the smartphone software with the left image being of the main tab for personal files, the central image being of the screencast tab to retrieve contents from a second device, and the right image being of the streaming tab to play content from the internet.

FIG. 18 shows the available tabs of the prototype in the smartphone software, with the left image being of a Main tab retrieving personal video files from the device storage, with the central image being of a Screencast tab to retrieve contents from a second device running the software, and with the right image being of a Streaming tab to play videos from the internet. More specifically, the default home tab is set for playback of locally stored video files (the left image). In his case, the system can retrieve all the video files in the smartphone and shows a preview frame from each of them to aid selection. Navigation through the three different modes is performed by selection of the desired tab from the menu at the bottom of the screen.

FIG. 19 shows a dichoptic presentation of a playback of user selected video during the therapy mode. Note that after a head gesture the playback menu is visible and the selected button shows a loading bar to help the user understanding when the tap gesture is performed.

It is possible to modify all the parameters of the vision therapy from the software and also remotely by providing the parameters through a configuration/prescription proprietary file recognized by the vision therapy system. A doctor remotely or in some cases the user is allowed to change vergence demand, vergence step, inter-pupillary and vertex distance to calibrate the headset, as well as the frequency of vergence changes. As additional parameters more controls are included for the suppression check protocol. The user can receive the prescription file from the doctor and apply it automatically when opening it with the vision therapy system.

The system can provide convergence exercises accordingly to the severity of the binocular disorder. After the user selects his desired video source, the system will start showing two videos that will first go aside and then go toward the middle simultaneously and repeatedly at a specific moving step and at a specific time interval calculated from the input parameters and the user head gesture feedback reporting fusional breakpoint. The pattern of motion is shown in FIGS. 20 and 21.

Figure 20:
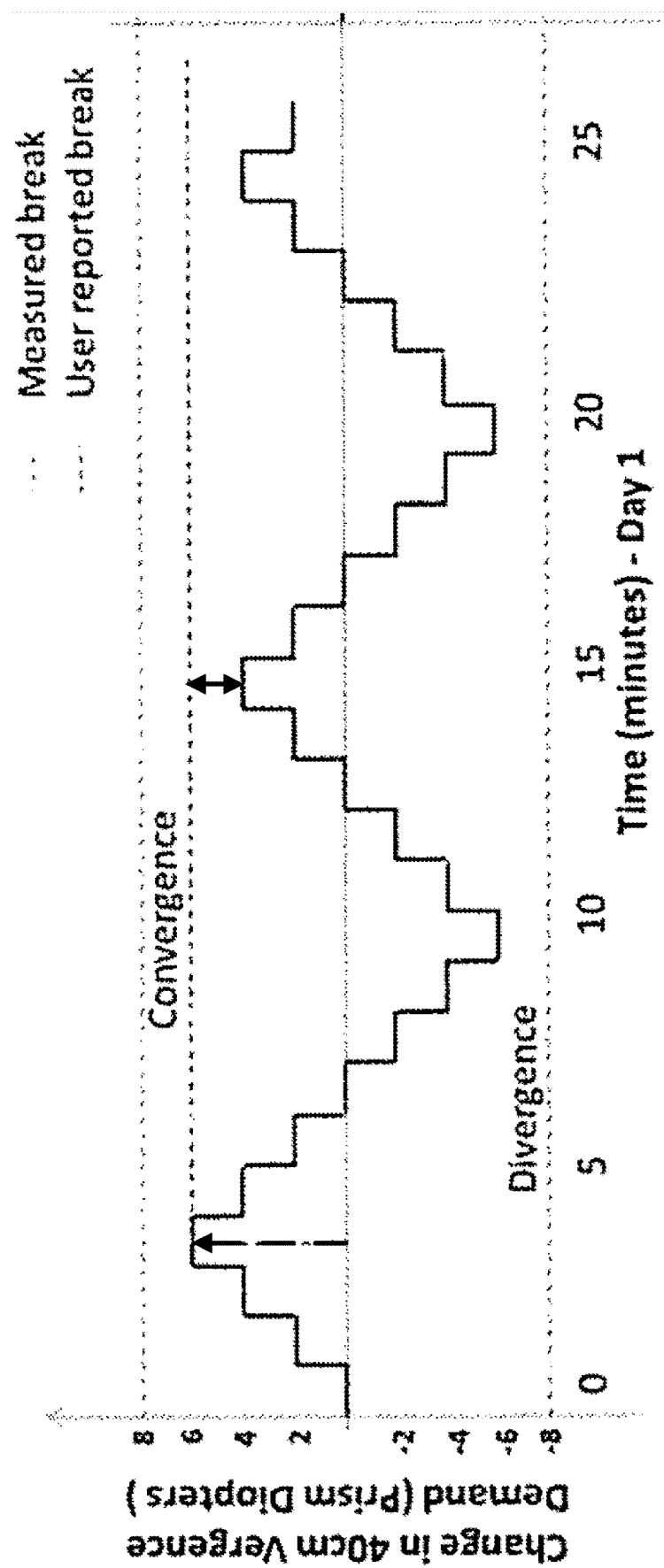
FIG. 20 shows a graph of the training course for the first day.
Figure 21:
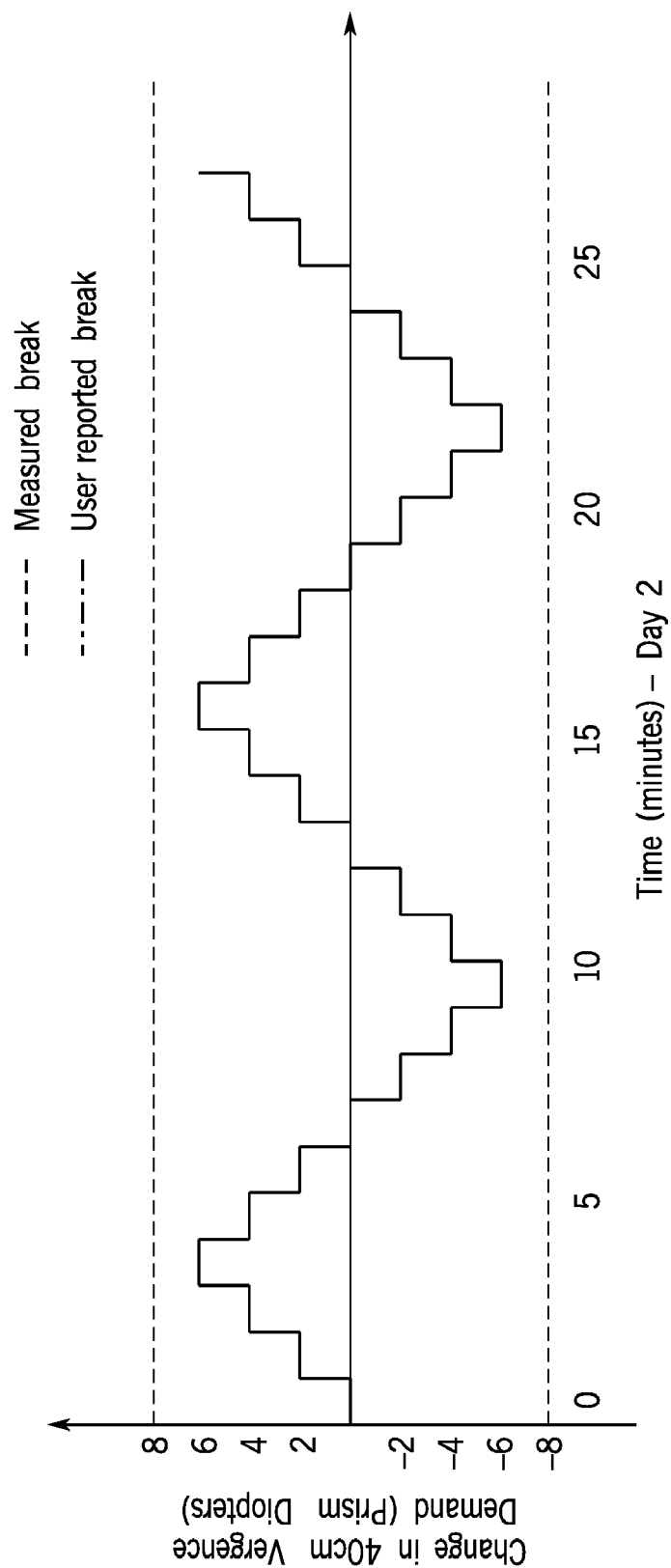
FIG. 21 shows a graph of the training course for the second day.

FIGS. 20 and 21 show the training course will end when the user secondly presses the button or when the main activity loses the focus, which happens when the user enters the Settings page or goes back to home screen. If the training duration is shorter than the designated value, like 30 seconds, this move process will not be regarded as a training. Additionally, if the patient at any time of the therapy, reports discomfort (also including double vision) by the head gesture or tapping the screen, the maximum vergence demand is reduced to a lower value temporarily. The amplitude and duration of the temporary vergence demand reduction requested by the user is controlled via a parameter from the doctor to avoid poor efficacy of the therapy. As shown, the dotted arrow of FIG. 20 indicates the location in time (e.g., between 0 and 5 minutes) that the user has pressed the button to indicate a break. In this case, the device, on the next convergence exercise (e.g., at around 15 minutes) decreased the maximum convergence value by a threshold amount (such as 2 units in the graph of FIG. 20).

There are more parameters to customize the vision therapy prescription for a patient: interval—the time interval in between moves of the videos from one vergence demand to the other, and forget: the number of times the patient can report a discomfort via head gesture before influencing the prescribed protocol (max vergence values correction). The reporting of discomfort can also be performed via pressing a specific BREAK button on a Bluetooth controller. Based on the patients' feedback, the doctor can monitor the progress remotely through a client software that reads patient automatic uploads to the cloud and also prescribes changes in the vergence demand, the time intervals and the forget parameter. The doctor can input those parameters into a new binocular vision therapy (BVT) file (customized file type).

The suppression control module is a way to signal the software running the vision therapy to activate a central stimulus to make sure that the user is not suppressing any images between left and right frame when playing videos in the headset. The control module is a flask application that maintains a temporary list of active devices within the same Wi-Fi network and removes them when not available. The whole module is based on API requests sent from the headset device to the web server and vice versa. As the user enters the SSID name of the Wi-Fi a list of available devices is returned and sorted based on the name. On the web interface an "Activate" button makes the cursor appear in the therapy video played in the headset, the "Deactivate" button removes it. Front end requests are sent via AJAX programming.

All therapy session times and parameters, including head gesture reports are stored locally in a database and can be shared with the remote doctor to monitor progresses, can monitor the user. A widely available and effective approach to in-home CI training could in theory overcome these cost and convenience barriers to care. With conventional home-based therapy paradigms, this requirement is difficult to meet because vision therapy requires repeated, tedious vergence exercise over a lengthy period of time.

An inexpensive home-based VT system and method is provided that promotes increased compliance while allowing remote monitoring of therapy progress could therefore deliver a game-changing improvement in CI treatment efficacy while lowering barriers to access.

Phoria testing: A phoria (or latent eye deviation) only appears when binocular viewing is broken and the two eyes are no longer looking at the same object. In clinic, the gold standard for phoria measurement is the Von Graefe test performed with a phoropter. A letter Z is shown to the left and the right eye inducing dissociation of the views horizontally and vertically via diffraction of the light through Risley prisms. The patient experiences an initial view of two letter Zs separated horizontally and vertically. The specialized eye doctor varies manually the power of the horizontal prism to move the stimulus on the right eye until the patient perceives it aligned with the one on the left. The amount of prism power administered at the time of alignment is then recorded as horizontal phoria. The EyeBiT App mimics this exact same behavior but virtually producing the images on the smartphone screen for the left and right eye and automatically shifting the letters horizontally by a calibrated amount equivalent to the prism diopters used in the phoropter. The system calibration is performed via utilizing the physical measures of the headset and the patient interpupillary distance. In the case of the EyeBiT App (e.g., the system of the example), the patient is asked to report when the letters are perceived aligned through the press of a reporting button on the headset. The measurement is repeated 5 times and the final output is the average of all.

Figure 22:
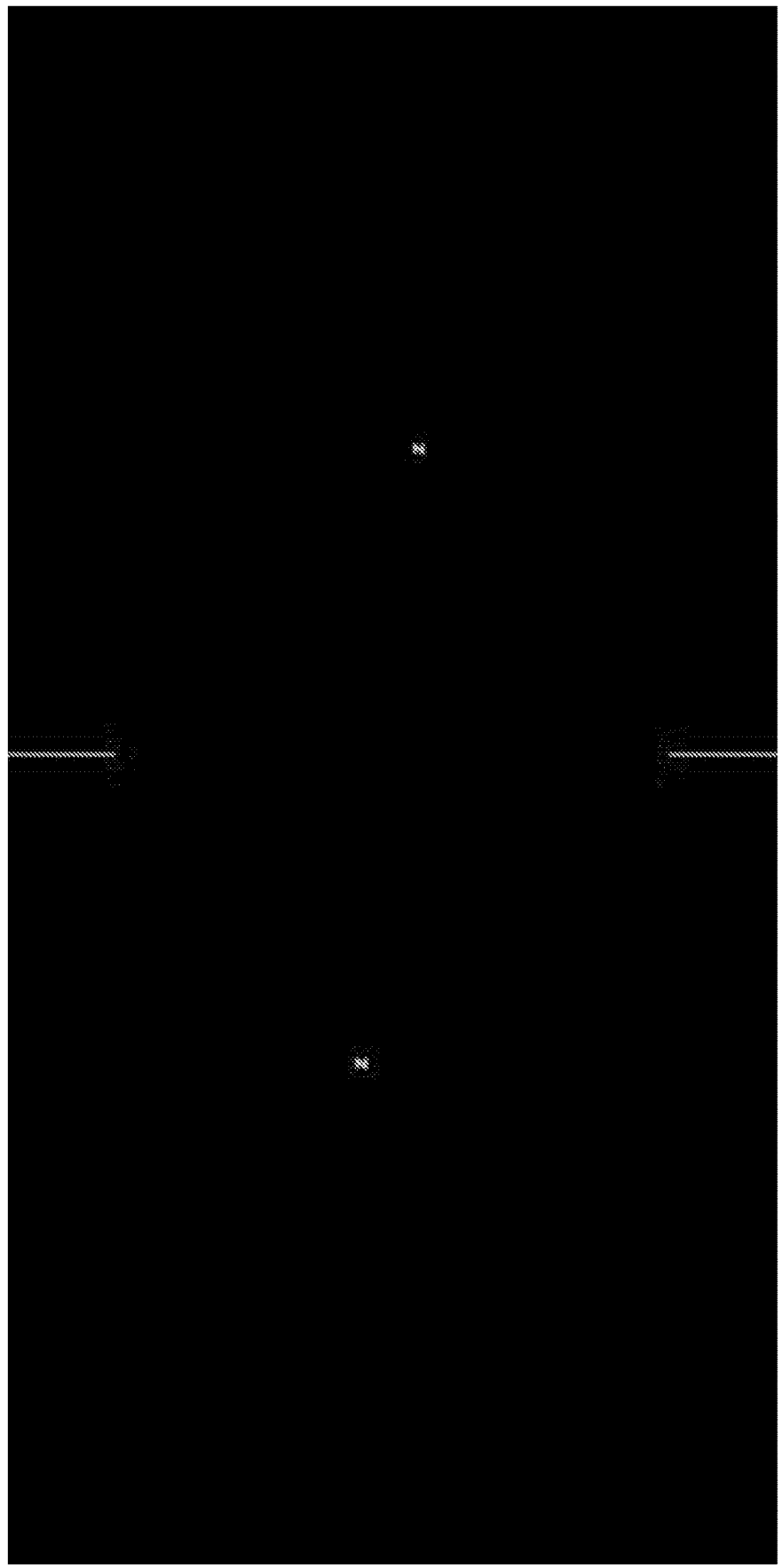
FIG. 22 shows screenshots of the binocular vision measurement functionalities from measurement of horizontal phoria with the simulated Von Graefe method.

FIG. 22 shows screenshots of the binocular vision measurement functionalities from measurement of horizontal phoria with the simulated Von Graefe method. Left and right views show a letter Z that synchronously moves toward the patient nose or separates from it.

Figure 23:
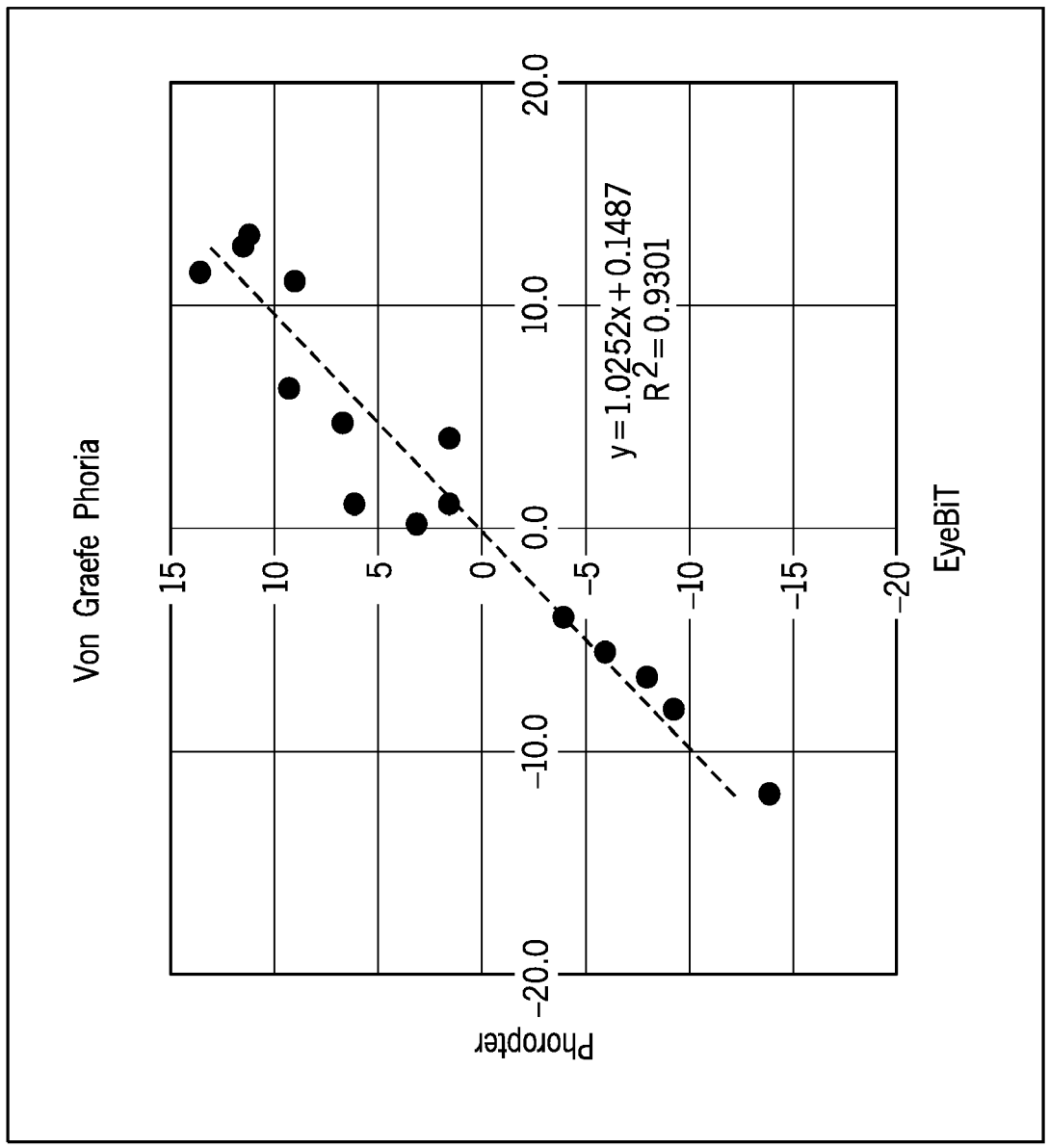
FIG. 23 shows a graph demonstrating the correlation between the EyeBiT phoria measurements from the prototype system and Von Graefe phorias measured at the phoropter by an optometrist.

FIG. 23 shows a graph demonstrating the correlation between EyeBiT phoria measurements and Von Graefe phorias measured at the phoropter by an optometrist.

In some non-limiting examples, a system for therapy and assessment of binocular vision disorders is provided. The system can include a computing device, comprising a computer processor, at least one memory module capable of storing computing instructions, at least one display screen, and at least one capability for wireless communication with other computing devices. The system can include an optional second computing device comprising a second computer processor, at least one memory module capable of storing computing instructions, at least one display screen, and at least one capability for wireless communication with other computing devices. The system can include a head-mounted set into which the first computing device is either pre-assembled or inserted by a user, the display screen oriented towards the eyes of the user, and which incorporates a binocular optical system allowing the user to focus clearly on the display screen. In some non-limiting examples, software resident in the memory of the first computing device causes the first computer processor to retrieve a user selected video content from local memory, the internet, or the optional secondary device, transforming the stream into an automated stimulus for binocular vision therapy or assessment.

In some non-limiting examples, the software resident in the memory of the computing device causes the first computer processor to process visual content received as a consequence of the screen-cast protocol executed by the secondary computing device so as to generate a pair of dichoptic views of the screen-casted visual content and to separately display the dichoptic images to the left and the right eyes of the user on separate areas of the first computing device display screen, accompanied by audio content when available.

In some non-limiting examples, the software resident in the memory of the computing device causes the first computer processor to execute at least one sequence of binocular vision therapy or binocular vision assessment protocol in which the binocular vergence demand is altered to the user by incremental alterations of the relative position in the horizontal axis between the two dichoptic images, or occlusion of one or more portions of at least one of the two images, or a combination of two or more of these several attributes.

In some non-limiting examples, the software resident in the memory of the computing device causes the first computer processor to receive, at any time during vision therapy or assessment and not linked by consequence to any pre-determined protocol step or magnitude of binocular vision demand, input from the user to signal that a boundary condition has been exceeded, the boundary condition being the experience by the user of loss of binocular image fusion or discomfort, and thereby to record in the computer processor or memory the magnitude of vision demand at which binocular image fusion was lost and to trigger an automated change to the vision therapy protocol so as to adjust the magnitude of binocular vision demand presented to the user.

In some non-limiting examples, the software resident in the memory of the computing device causes the first computer processor to document, for each therapy protocol performed, at least one record of protocol completion by the user and at least one record of binocular vision assessment of the user in a progress tracker database, where the database is employed to communicate values and trends of such data over time to aid in assessment of user progress in binocular vision therapy by a remote person.

In some non-limiting examples, the software resident in the memory of the computing device causes the first computer processor to monitor, for eventual suppression of one of the two dichoptic images by the user's brain via means of embedded stimuli in the user selected content that can be activated or deactivated remotely via a web interface from a person monitoring the patient.

In some non-limiting examples, the first computing device is a smartphone, tablet computing device, or any other screen-bearing mobile computing device capable of wireless communication.

In some non-limiting examples, the second optional computing device is a personal computer, smartphone, tablet computing device, or any other screen-bearing mobile computing device capable of wireless communication.

In some non-limiting examples, the screen-cast visual content used for generation by the first computing device of dichoptic views includes any visual content generated by the same first device or by an optional second computing device and viewable on said device's display screen, including but not limited to a) views of internet sites (web pages), b) video games performed on either computer or mobile device platforms, c) static images (photo galleries or other sources), d) video content (derived from digital video disk, fixed storage, camera feeds, or internet streaming, or other sources), e) mobile device applications, or f) computer software applications (word processing, spreadsheet, slide presentation, or other application).

In some non-limiting examples, the screen cast protocol is accomplished by a screen mirroring protocol such that visual content displayed by the second computing device is replicated on the display screen of the first computing device.

In some non-limiting examples, the screen cast protocol is accomplished by transmission of compressed digital content from the second computing device to the first computing device whereupon the first computing device processes the content for purposes of display.

In some non-limiting examples, the vision demand for binocular vision therapy or assessment is an image vergence demand for treatment of convergence insufficiency, whereby the treatment protocol comprises a series of incremental changes to relative positioning of the first and second dichoptic images displayed to the left and the right eyes of the user.

In some non-limiting examples, the vision demand for binocular vision therapy or assessment employs partial occlusion of at least one image for checking vision suppression, whereby the treatment protocol comprises a series of incremental changes to the size and/or position of the occluded portion of at least one of the first and second dichoptic images displayed to the left and the right eyes of the user.

In some non-limiting examples, the selection by the user of visual content for binocular vision therapy and assessment and control by the user of the initiation, interaction, pausing, and termination of viewing of the content may be performed by at least one of the following: a head gesture, a voice command, a user-actuated control integral to the head-mounted display device, a touch gesture on the screen of the first computing device, or use of a hand actuated controller connected to the second computing device via wireless communication or via direct connection.

In some non-limiting examples, input by the user to control attributes of, or provide feedback to, a binocular vision therapy protocol or to a binocular vision performance assessment may be performed by means of at least one of the following: a head gesture, a voice command, a user-actuated controls integral to the head-mounted display device, a touch gesture on the screen of the first computing device, a use of a handheld remote controller connected to the second computing device via wireless communication or via direct connection.

In some non-limiting examples, a report comprising at least one result of binocular vision performance assessment and/or at least one result of compliance with a binocular vision therapy protocol is transmitted via privacy-secured telecommunication for viewing by or an individual overseeing the user's vision treatment and/or assessment, whereby the use of telecommunication may include but is not limited to: wireless digital communication, email, text messaging, file upload to a server, and whereby the telecommunication can comprise either a direct transmission to the intended recipient or a transmission to a computer server for purposes of storage and subsequent retrieval.

In some non-limiting examples, changes to the user's vision treatment or assessment protocol are communicated to the first computing device via wireless digital communication from an individual overseeing the user's vision treatment and/or assessment.

Although the invention has been described and illustrated in the foregoing illustrative non-limiting examples, it is understood that the present disclosure has been made only by way of example, and that numerous changes in the details of implementation of the invention can be made without departing from the spirit and scope of the invention, which is limited only by the claims that follow. Features of the disclosed non-limiting examples can be combined and rearranged in various ways.

Furthermore, the non-limiting examples of the disclosure provided herein are not limited in application to the details of construction and the arrangement of components set forth in the following description or illustrated in the following drawings. The invention is capable of other non-limiting examples and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

Also, the use the phraseology and terminology used herein is for the purpose of description and should not be regarded as limiting. The use of "right", "left", "front", "back", "upper", "lower", "above", "below", "top", or "bottom" and variations thereof herein is for the purpose of description and should not be regarded as limiting. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

Unless otherwise specified or limited, phrases similar to "at least one of A, B, and C," "one or more of A, B, and C," and the like, are meant to indicate A, or B, or C, or any combination of A, B, and/or C, including combinations with multiple or single instances of A, B, and/or C.

In some non-limiting examples, aspects of the present disclosure, including computerized implementations of methods, can be implemented as a system, method, apparatus, or article of manufacture using standard programming or engineering techniques to produce software, firmware, hardware, or any combination thereof to control a processor device, a computer (e.g., a processor device operatively coupled to a memory), or another electronically operated controller to implement aspects detailed herein. Accordingly, for example, non-limiting examples of the invention can be implemented as a set of instructions, tangibly embodied on a non-transitory computer-readable media, such that a processor device can implement the instructions based upon reading the instructions from the computer-readable media. Some non-limiting examples of the invention can include (or utilize) a device such as an automation device, a special purpose or general purpose computer including various computer hardware, software, firmware, and so on, consistent with the discussion below.

The term "article of manufacture" as used herein is intended to encompass a computer program accessible from any computer-readable device, carrier (e.g., non-transitory signals), or media (e.g., non-transitory media). For example, computer-readable media can include but are not limited to magnetic storage devices (e.g., hard disk, floppy disk, magnetic strips, and so on), optical disks (e.g., compact disk (CD), digital versatile disk (DVD), and so on), smart cards, and flash memory devices (e.g., card, stick, and so on). Additionally, it should be appreciated that a carrier wave can be employed to carry computer-readable electronic data such as those used in transmitting and receiving electronic mail or in accessing a network such as the Internet or a local area network (LAN). Those skilled in the art will recognize many modifications may be made to these configurations without departing from the scope or spirit of the claimed subject matter.

Certain operations of methods according to the invention, or of systems executing those methods, may be represented schematically in the FIGS. or otherwise discussed herein. Unless otherwise specified or limited, representation in the FIGS. of particular operations in particular spatial order may not necessarily require those operations to be executed in a particular sequence corresponding to the particular spatial order. Correspondingly, certain operations represented in the FIG., or otherwise disclosed herein, can be executed in different orders than are expressly illustrated or described, as appropriate for particular non-limiting examples of the invention. Further, in some non-limiting examples, certain operations can be executed in parallel, including by dedicated parallel processing devices, or separate computing devices configured to interoperate as part of a large system.

As used herein in the context of computer implementation, unless otherwise specified or limited, the terms "component," "system," "module," and the like are intended to encompass part or all of computer-related systems that include hardware, software, a combination of hardware and software, or software in execution. For example, a component may be, but is not limited to being, a processor device, a process being executed (or executable) by a processor device, an object, an executable, a thread of execution, a computer program, or a computer. By way of illustration, both an application running on a computer and the computer can be a component. One or more components (or system, module, and so on) may reside within a process or thread of execution, may be localized on one computer, may be distributed between two or more computers or other processor devices, or may be included within another component (or system, module, and so on).

Although the description above, with regard to the processes above, has been framed with respect to specific computing devices implementing these processes (as appropriate), it is also understood that a non-transitory computer-readable medium (e.g., such as the article of manufacture described above) can store computer-executable code for the processes described above. For example, process 300, the sub process 302, the process 400 (or others) can be effectively stored on the non-transitory computer-readable medium.

As used herein, the term, "controller" and "processor" and "computer" include any device capable of executing a computer program, or any device that includes logic gates configured to execute the described functionality. For example, this may include a processor, a microcontroller, a field-programmable gate array, a programmable logic controller, and the like. As another example, these terms may include one or more processors and memories and/or one or more programmable hardware elements, such as any of types of processors, CPUs, microcontrollers, digital signal processors, or other devices capable of executing software instructions.

The invention claimed is:

1. A system for treating or detecting binocular vision disorders of a patient, the system comprising:
    a display;
    a computing device in communication with the display, the computing device being configured to:
        present to the patient, on the display, a first video that spans a first portion of the display;
        present to the patient, on the display, a second video that spans a second portion of the display, wherein the first video spanning the first portion of the display does not overlap with the second video spanning the second portion of the display, and wherein the first video spanning the first portion of the display is separated from the second video spanning the second portion of the display to form a dichoptic presentation;
        translate the first video on the display to a first different location on the display than the first portion of the display according to a predetermined pattern selected to alter a binocular vergence demand on the patient; and
        translate the second video on the display to a second different location on the display than the second portion of the display according to the predetermined pattern selected to alter the binocular vergence demand on the patient.

2. The system of claim 1, wherein the computing device is further configured to:
    receive a user input from the patient; and
    at least one of, generate a report for the patient, based on the user input, or adjust the predetermined pattern based on the user input.

3. The system of claim 1, wherein the display has a vertical axis that vertically bisects the display, wherein translating the first video and translating the second video according to the predetermined pattern includes the computing device being further configured to:
    wait a time period prior to translating the first video;
    wait another time period prior to translating the second video,
    wherein the first video is translated a first distance relative to the vertical axis, and the second video is translated a second distance relative to the vertical axis, and
    wherein the magnitude of the first distance is substantially identical to the magnitude of the second distance.

4. The system of claim 3, wherein the first video is translated horizontally the first distance toward the vertical axis, and
    wherein the second video is translated horizontally the second distance toward the vertical axis.

5. The system of claim 3, wherein the first video is translated horizontally the first distance away from the vertical axis, and
    wherein the second video is translated horizontally the second distance away from the vertical axis.

6. The system of claim 1, further comprising a lens positioned in front of, and optionally coupled to the display, and
    wherein the first video is projected through the lens and to only one eye of the patient.

7. The system of claim 6, wherein the lens is a first lens, and further comprising a second lens positioned in front of, and optionally coupled to the display, and
    wherein the second video is projected through the second lens and to only the other eye of the patient.

8. The system of claim 7, further comprising a head mounted display having the display, and
    wherein the first lens, and the second lens, are part of the head mounted display.

9. The system of claim 1, wherein the first video and the second video are substantially identical.

10. The system of claim 1, wherein the computing device is further configured to cause the display to occlude a portion of the second video.

11. The system of claim 1, wherein the computing device is further configured to:
    present, on the display, a first dichoptic mark on the first video; and
    present, on the display, a second dichoptic mark on the second video.

12. The system of claim 11, wherein the first dichoptic mark is centrally located on the first video, and
wherein the second dichoptic mark is centrally located on the second video.

13. The system of claim 11, further comprising a user interface in communication with the computing device, and wherein the computing device is further configured to:
receive, via the user interface, a user input indicative of the user being unable to properly fuse the first dichoptic mark with the second dichoptic mark.

14. A method for treating or detecting binocular vision disorders of a patient, the method comprising:
presenting to the patient, on a display, first content that spans a first portion on the display;
presenting to the patient, on the display, second content that spans a second portion of the display, wherein the first portion of content spanning the first portion of the display does not overlap with the second content spanning the second portion of the display, and wherein the first content spanning the first portion of the display is separated from the second content spanning the second portion of the display to form a dichoptic presentation;
translating the first content, on the display, to a first different location on the display than the first portion of the display according to a predetermined pattern selected to alter a binocular vergence demand on the patient; and
translating the second content, on the display, to a second different location on the display than the second content on the display according to the predetermined pattern selected to alter the binocular vergence demand on the patient.

15. The method of claim 14, further comprising receiving a user input from the patient; and further comprising at least one of:
generating a report for the patient based on the user input; and
adjusting the predetermined pattern, based on the user input.

16. The method of claim 14, wherein the display has a vertical axis that vertically bisects the display, and further comprising:
waiting a time period prior to translating the first content;
waiting another time period prior to translating the second content,
wherein the first content is translated a first distance relative to the vertical axis, and the second content is translated a second distance relative to the vertical axis,
wherein the magnitude of the first distance is substantially identical to the magnitude of the second distance, and
wherein the time period and the another time period are substantially identical.

17. The method of claim 14, further comprising:
presenting, on the display, a first dichoptic mark on the first content; and
presenting, on the display, a second dichoptic mark on the second content.

18. The method of claim 17, wherein the first dichoptic mark is centrally located on the first content, and
wherein the second dichoptic mark is centrally located on the second content.

19. The method of claim 17, further comprising receiving, via a user interface, a user input indicative of the user being unable to properly fuse the first dichoptic mark with the second dichoptic mark.

20. The method of claim 14, wherein the display has a vertical axis that vertically bisects the display;
wherein the first content is translated horizontally a first distance away from the vertical axis;
wherein the second content is translated horizontally a second distance away from the vertical axis;
wherein a magnitude of the first distance is substantially similar to a magnitude of the second distance; and
wherein the horizontal translation of the first content and the second content increases a divergence demand of the patient.

21. The method of claim 14, wherein the display has a vertical axis that vertically bisects the display;
wherein the first content is translated horizontally a first distance towards the vertical axis;
wherein the second content is translated horizontally a second distance towards the vertical axis;
wherein a magnitude of the first distance is substantially similar to a magnitude of the second distance; and
wherein the horizontal translation of the first content and the second content increases a convergence demand of the patient.

22. A non-transitory computer-readable medium storing computer-executable code, comprising code for causing a computing device to:
present to a patient, on a display, first content that spans a first portion of the display;
present to the patient, on the display, second content that spans a second portion of the display, wherein the first content does not overlap with the second content, and wherein the first content and the second content form a dichoptic presentation;
translate the first content on the display according to a predetermined pattern selected to alter a binocular vergence demand on the patient; and
translate the second content on the display according to the predetermined pattern selected to alter a binocular vergence demand on the patient, and
wherein the first content and the second content are substantially identical.

* * * * *